(12) United States Patent  
Amitani et al.

(10) Patent No.: US 7,508,915 B2  
(45) Date of Patent: Mar. 24, 2009

(54) RADIOGRAPHYING SYSTEM AND RADIATION IMAGE DETECTING DEVICE

(75) Inventors: Kouji Amitani, Tachikawa (JP); Mamoru Umeki, Hachioji (JP)

(73) Assignee: Konica Minolta Medical & Graphic Inc., Tokyo (JP)

( * ) Notice: Subject to any disclaimer, the term of this patent is extended or adjusted under 35 U.S.C. 154(b) by 0 days.

(21) Appl. No.: 11/999,357

(22) Filed: Dec. 5, 2007

(65) Prior Publication Data  
US 2008/0247513 A1 Oct. 9, 2008

(30) Foreign Application Priority Data  
Dec. 11, 2006 (JP) ............................. 2006-333019  
Jan. 10, 2007 (JP) ............................. 2007-002240

(51) Int. Cl.  
*H05G 1/64* (2006.01)

(52) U.S. Cl. ...................................... 378/98.8; 378/62

(58) Field of Classification Search ............... 378/4–20, 378/62, 98.8  
See application file for complete search history.

(56) References Cited  
U.S. PATENT DOCUMENTS  
6,348,793 B1 2/2002 Balloni et al.

| | | |
|---|---|---|
| 2004/0066900 A1 | 4/2004 | Motoki et al. |
| 2004/0071263 A1 | 4/2004 | Motoki et al. |
| 2004/0071369 A1 | 4/2004 | Onishi |
| 2004/0088194 A1 | 5/2004 | Moriyama |
| 2004/0089710 A1 | 5/2004 | Moriyama |
| 2005/0008262 A1 | 1/2005 | Komiya et al. |
| 2006/0034427 A1 | 2/2006 | Brooks |
| 2006/0184943 A1 | 8/2006 | Delmonego et al. |

FOREIGN PATENT DOCUMENTS

| | | |
|---|---|---|
| EP | 1 389 769 A2 | 2/2004 |
| EP | 1 406 197 A2 | 4/2004 |
| EP | 1 406 202 A2 | 4/2004 |
| EP | 1 416 320 A2 | 5/2004 |
| EP | 1 416 418 A2 | 5/2004 |
| EP | 1 484 707 A3 | 5/2006 |
| JP | 2006-122304 A | 5/2006 |

OTHER PUBLICATIONS

English Language extended European Search Report dated Jul. 7, 2008 issued in counterpart European Appln. No. EP 07 25 4689.

*Primary Examiner*—Courtney Thomas  
(74) *Attorney, Agent, or Firm*—Frishauf, Holtz, Goodman & Chick, P.C.

(57) ABSTRACT

A radiographing system wherein, in the "Receiving" state of having received the radiographing order from one control terminal apparatus, an FPD does not receive other radiographing reservation, or in the "Receiving" state of having received the radiographing order from one control terminal apparatus, a management server does not receive any other radiographing order.

12 Claims, 17 Drawing Sheets

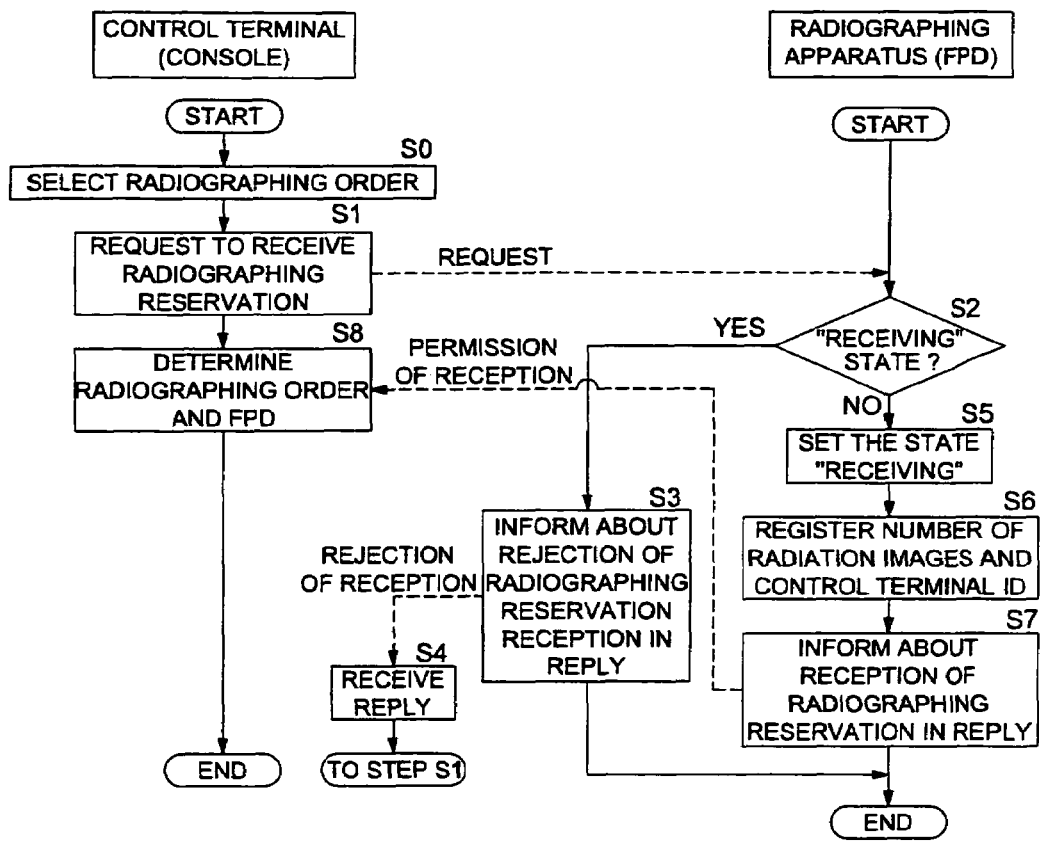

| | p1 | p2 | p3 | p4 | p5 | p6 | p7 | p8 |
|---|---|---|---|---|---|---|---|---|
| | RADIOGRAPHING ORDER ID | PATIENT ID | PATIENT NAME | SEX | AGE | DEPARTMENT OF DIAGNOSIS | REGION | DIRECTION |
| | 61201001 | 100085 | ICHIRO SUZUKI | MALE | 25 | SURGERY | CHEST | FRONT A-P |
| | 61212002 | 100085 | ICHIRO SUZUKI | MALE | 25 | SURGERY | CHEST | SIDE |
| | 61223003 | 100125 | HANAKO YAMADA | FEMALE | 55 | OBSTETRICS | BREAST | MLO-R |
| | 61234004 | 100125 | HANAKO YAMADA | FEMALE | 55 | OBSTETRICS | BREAST | MLO-L |
| | 61245005 | 100125 | HANAKO YAMADA | FEMALE | 55 | OBSTETRICS | BREAST | CC-L |
| | 61256006 | 100125 | HANAKO YAMADA | FEMALE | 55 | OBSTETRICS | BREAST | CC-R |
| | 61267007 | 100320 | JIRO SATO | MALE | 15 | ORTHOPEDICS | LEG | L |
| | 61278008 | 100325 | EISAKU YOSHIDA | MALE | 60 | ORTHOPEDICS | HAND | L |
| | 61289009 | 100330 | ICHIRO WATANABE | MALE | 45 | ORTHOPEDICS | CHEST | FRONT A-P |

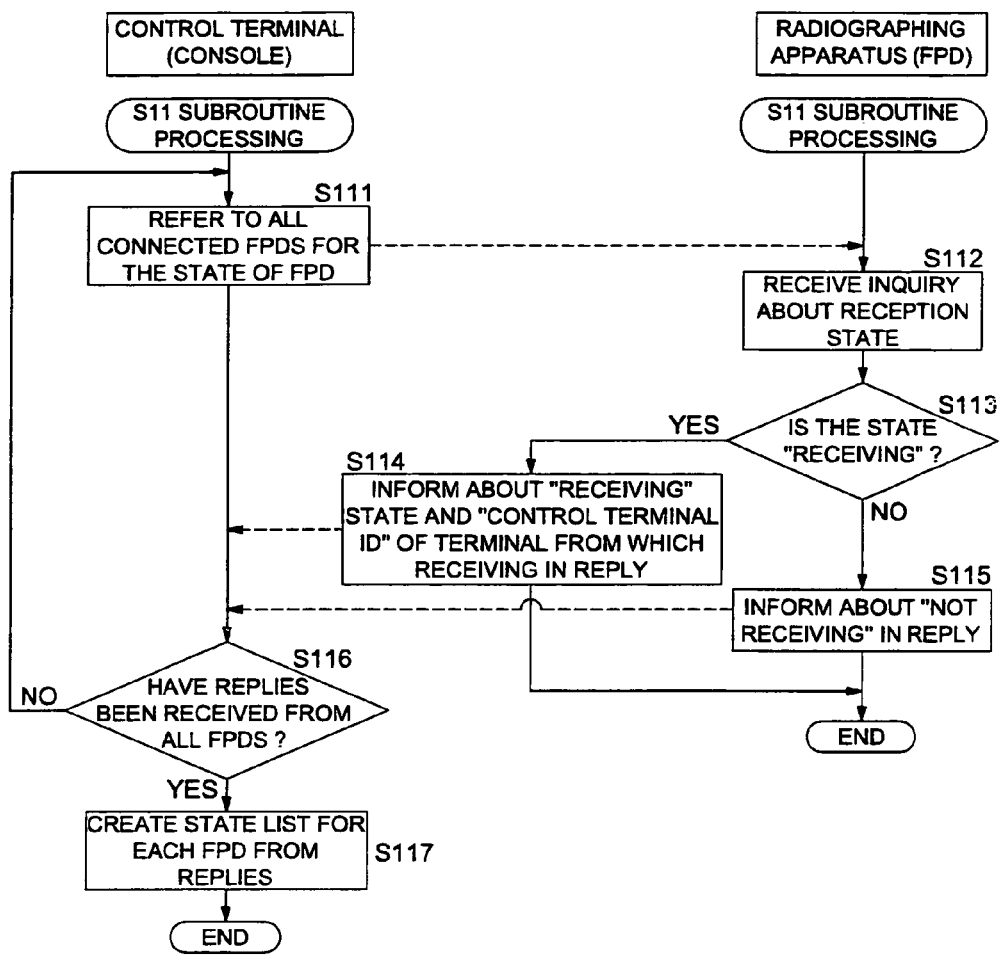

RADIOGRAPHYING SYSTEM AND RADIATION IMAGE DETECTING DEVICE

This application is based on Japanese Patent Application Nos. 2006-333019 filed on Dec. 11, 2006 and 2007-002240 filed on Jan. 10, 2007 in Japanese Patent Office, the entire content of which is hereby incorporated by reference.

BACKGROUND OF THE INVENTION

The present invention relates to a radiographing system for applying radiation to a subject to be examined to obtain radiation image data based on the amount of radiation having passed through the subject, particularly to a radiographing system and a radiation image detecting device connected over the communication line.

In recent years, a digital type radiation image detecting device is used to capture a radiation image by applying radiation to a subject and detecting the radiation having passed through the subject. The radiation image detecting device of this type is exemplified by a so-called FPD (Flat Panel Detector).

In one example of the FPD, a plurality of detecting elements are arranged on a substrate in a two-dimensional array, and the radiation having passed through the subject is applied to a phosphor (scintillator). The visible light emitted in conformity to the amount of radiation applied is converted into an electric charge by a detecting element, and is stored in a capacitor. The electric charge stored in the capacitor is read to get a radiation image. Such an FPD is characterized in that the radiation image can be obtained immediately after radiographing.

In recent years, the HIS (Hospital Information System) as a system for centralized management of the patient diagnostic information and accounting information, and the RIS (Radiology Information System) as a system for management of the radiographing order information in the department of radiology have been introduced to provide an extra convenience in information utilization and an increased speed in various forms of processing. The control terminals of various types of radiation image radiographing apparatuses and radiographing apparatuses are connected with the RIS and HIS over the network such as the LAN arranged in a hospital.

A radiation image system is disclosed in the Patent Document 1 wherein a plurality of control terminals (consoles) and a plurality of FPD with communication functions are connected to such a network in the hospital. In the radiation image system described in the Patent Document 1, in order to enhance the efficiency of verifying the image by a radiographing technician or doctor, a radiographing order is sent to the selected FPD from the control terminal-before radiographing and is registered therein. After radiographing, a radiation image is sent from the FPD to the control terminal wherein the registration was made. This procedure allows the operator to go back to the control terminal wherein the radiographing order was registered, after radiographing, whereby the radiation image can be verified.

A portable cassette type FPD allows a plurality of radiation images to be stored in the internal memory. Thus, a plurality of radiographing orders can be registered in one operation, and a plurality of radiographing operations can be performed on a continuous basis.

A plurality of radiographing orders can be registered in such an FPD. Therefore, in a radiation image system wherein a plurality of control terminals and a plurality of FPDs are connected over the same network, radiographing reservations of different patients selected by each of technicians may be registered unintentionally in one and the same FPD successively by a plurality of technicians from different control terminals. This may cause a serious accident of confusing the correlation between the patient and radiation image.

[Patent Document 1] Japanese Unexamined Patent Application Publication No. 2006-122304

SUMMARY

An object of the present invention is to solve the aforementioned problems and to provide a radiographing system and a radiation image detecting device wherein a plurality of control terminals and a plurality of FPDs (radiation image detecting devices) are connected over one and the same communication line, and means are provided to avoid duplicated registration of radiographing reservations in one and the same FPD from a plurality of control terminals and to prevent confusion of a radiation image and corresponding patient.

The aforementioned object of the present invention can be achieved by the following embodiments of invention:

(1) A radiographing system wherein a plurality of radiation image detecting devices for acquiring radiation image data based on the radiation having passed through a subject to be examined, and a control terminal apparatus for selecting a radiation image detecting device for performing radiographing, out of a plurality of the aforementioned radiation image detecting devices are connected over the communication line;

the aforementioned radiographing system being characterized in that, in the state of receiving of having received a radiographing reservation from a control terminal apparatus, the aforementioned radiation image detecting device rejects reception of other radiographing reservation.

(2) A radiographing system wherein a plurality of radiation image detecting devices for acquiring radiation image data based on the radiation having passed through a subject to be examined, and a plurality of control terminal apparatuses for selecting a radiation image detecting device for performing radiographing, out of a plurality of the aforementioned radiation image detecting devices are connected over the communication line;

the aforementioned radiographing system being characterized in that, in the state of receiving of having received a radiographing reservation from one of the control terminal apparatuses, the aforementioned radiation image detecting device rejects reception of radiographing reservation from other control terminal apparatuses.

(3) A radiation image detecting device, connected to a control terminal apparatus over the communication line, for acquiring radiation image data based on the radiation having passed through a subject to be examined, the aforementioned radiation image detecting device being characterized by including:

a radiographing reservation receiving section for receiving radiographing reservation from the control terminal apparatus;

a radiographing state control section for setting the reception state to be a state of receiving when the aforementioned radiographing reservation receiving section has received radiographing reservation; and a reception control section that controls acquisition of the radiation image data related to the radiographing reservation received by the aforementioned radiographing reservation receiving section, and, if the reception state is the state of receiving, rejects reception of other radiographing reservation.

(4) A radiographing system including:

a control terminal apparatus for sending radiographing reservation; and a radiation image detecting device, connected with the aforementioned control terminal apparatus over the communication line, for acquiring radiation image data based on the radiation having passed through a subject to be examined;

the aforementioned radiographing system further including:

a radiographing reservation receiving section for receiving radiographing reservation for the radiation image detecting device;

a radiographing state control section which, when the aforementioned radiographing reservation receiving section has received radiographing reservation, determines that the reception state of this radiation image detecting device is a state of receiving;

a reception control section which, when the aforementioned reception state is the state of receiving, rejects reception of other radiographing reservation for this radiation image detecting device related to the radiographing reservation received by the aforementioned radiographing reservation receiving section.

BRIEF DESCRIPTION OF THE DRAWINGS

FIG. 1(*b*) is a schematic view representing part of the radiographing system in the second embodiment.

FIG. 4 is a diagram representing the control flow of the radiographing system in the embodiment.

FIG. 5 is a diagram showing an example of a plurality of radiographing orders.

FIG. 8 is a diagram representing the subroutine processing for creating an FPD state list.

FIG. 9 is a diagram representing an example of the FPD state list.

DETAILED DESCRIPTION OF THE PREFERRED EMBODIMENT

Figure 1A:
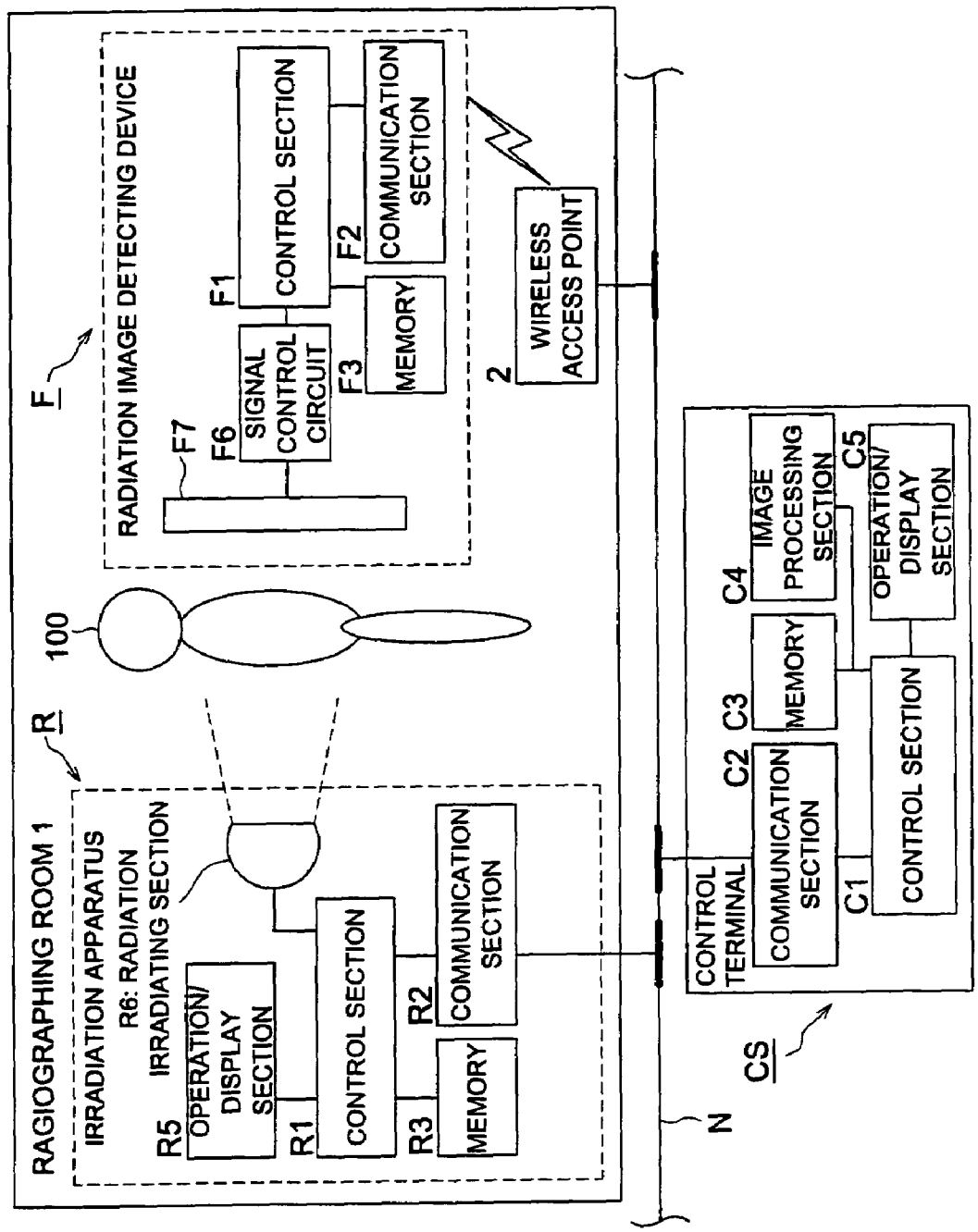
FIG. 1(*a*) is a schematic view representing part of the radiographing system in the first embodiment.

The following describes the embodiments of still further inventions:

(a) The radiographing system described in (1) or (2), wherein the aforementioned "Receiving" state is cancelled upon completion of reserved radiographing having been received in the aforementioned radiation image detecting device.

(b) The radiographing system described in (1), (2) or (a) wherein, upon completion of reserved radiographing having been received, the aforementioned radiation image detecting device sends the radiation image data to the control terminal apparatus whose radiographing reservation has been received.

(c) The radiographing system described in (1) or (2), wherein the aforementioned radiation image detecting device cancels the aforementioned "Receiving" state after completing reserved radiographing having been received, and transmission of all the radiation image data to the control terminal apparatus whose radiographing reservation has been received.

(d) The radiation image detecting device described in (3) further containing:

a receiving section for receiving the radiographing reservation and control terminal ID for identifying control terminal apparatus; and a storage section for storing the control terminal ID that identifies the control terminal apparatus whose radiographing reservation has been received, wherein, when the control terminal ID different from the control terminal ID stored in the aforementioned storage section has been received by the aforementioned receiving section, the aforementioned reception control section rejects such a radiographing reservation having been received from the control terminal apparatus which has a control terminal ID different from the control terminal ID stored.

(e) The radiation image detecting device described in (3) or (d) wherein the aforementioned "Receiving" state is cancelled after acquisition of radiation image data in the aforementioned radiographing state control section.

(f) A radiation image detecting device described in any one of (3), (d) and (e), wherein a transmission section for sending radiation image data is provided, and after radiation image data has been sent by the aforementioned transmission section, the aforementioned "Receiving" state is cancelled by the aforementioned radiographing state control section.

(g) A radiographing system described in (4) including, a receiving section for receiving radiographing reservation and the control terminal ID that identifies the control terminal apparatus having sent the radiographing reservation;

a storage section for storing a control terminal ID for identifying the control terminal apparatus that sends the radiographing reservation received by the aforementioned radiographing reservation receiving section and a detecting device ID for identifying the aforementioned radiation image detecting device related to the radiographing reservation received by the aforementioned radiographing reservation receiving section correlated with each other;

wherein, when there is agreement between the control terminal ID having received by the aforementioned receiving section and the control terminal ID stored in the aforementioned storage section, the aforementioned reception control section allows reception of other radiographing reservation having been received by the aforementioned receiving section for the radiation image detecting device corresponding to the detecting device ID correlated with the control terminal ID.

(h) The radiographing system described in (4) or (g) wherein, after the aforementioned radiation image detecting device has acquired the radiation image data, the aforementioned radiographing state control section cancels the aforementioned "Receiving" state in the radiation image detecting device.

(i) The radiographing system described in any one of (4), (g) and (h) wherein the radiation image detecting device contains a transmission section for sending radiation image data, and the aforementioned radiographing state control section cancels the aforementioned "Receiving" state in the radiation image detecting device after the aforementioned transmission section of the radiation image detecting device has sent radiation image data.

The following describes the embodiment of the present invention without the present invention being restricted thereto:

FIG. 1(a) is a schematic view representing a part of the radiographing system in the first embodiment. The radiographing system includes the irradiation apparatus R for irradiating a subject to be examined 100; a radiation image detecting device F for acquiring radiation image data based on the amount of radiation having passed through the subject; and a control terminal apparatus CS (hereinafter referred to as "control terminal") for performing various forms of operations. They are connected to the communication line N through the communication section of each apparatus. The communication system of the communication line is for example the LAN system based on the Ethernet (registered trademark) standard.

FIG. 1(b) is a schematic view representing a part of the radiographing system in the second embodiment. The radiographing system includes the irradiation apparatus R for irradiating a subject to be examined 100; a radiation image detecting device F for acquiring radiation image data based on the amount of radiation having passed through the subject; and a control terminal apparatus CS (hereinafter referred to as "control terminal CS") for performing various forms of operations; and a management server MS. They are connected to the communication line N through the communication section of each apparatus. The communication system of the communication line is the LAN system based on the Ethernet (registered trademark) standard.

[Irradiation Apparatus]

The irradiation apparatus R is provided with a control section R1, communication section R2, memory R3, operation/display section R5 and radiation-irradiation section R6.

The radiation irradiation section R6 has an anode made of heavy metal. When a high voltage of 20 kV through 150 kV, for example, is applied to the filament, electron beam is generated. When the electron beam is applied to the anode (target), radiation is generated. A fixed anode or a rotary anode characterized by excellent durability is used as an anode. The radiation used in the embodiment has a wavelength of about $1\times10^{-10}$ m.

The control section R1 is made up of a CPU, system memory and others. Various types of control are provided as the program stored in the system memory is executed by the CPU.

The communication section R2 of the irradiation apparatus R communicates with the radiation image detecting device F, control terminal CS and others over the communication line N (LAN).

[Radiation Image Detecting Device]

Figure 1:
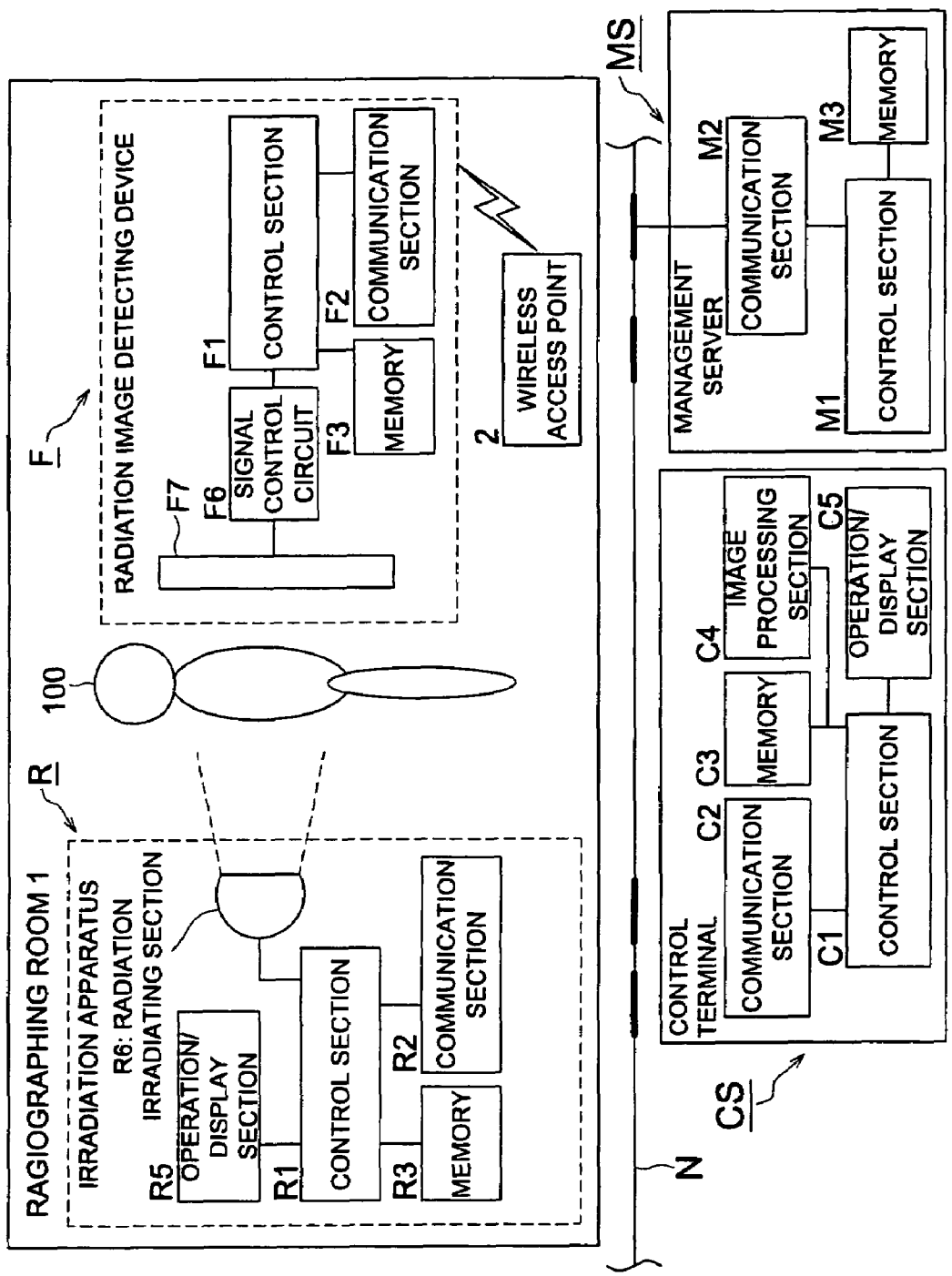
Figure 2:
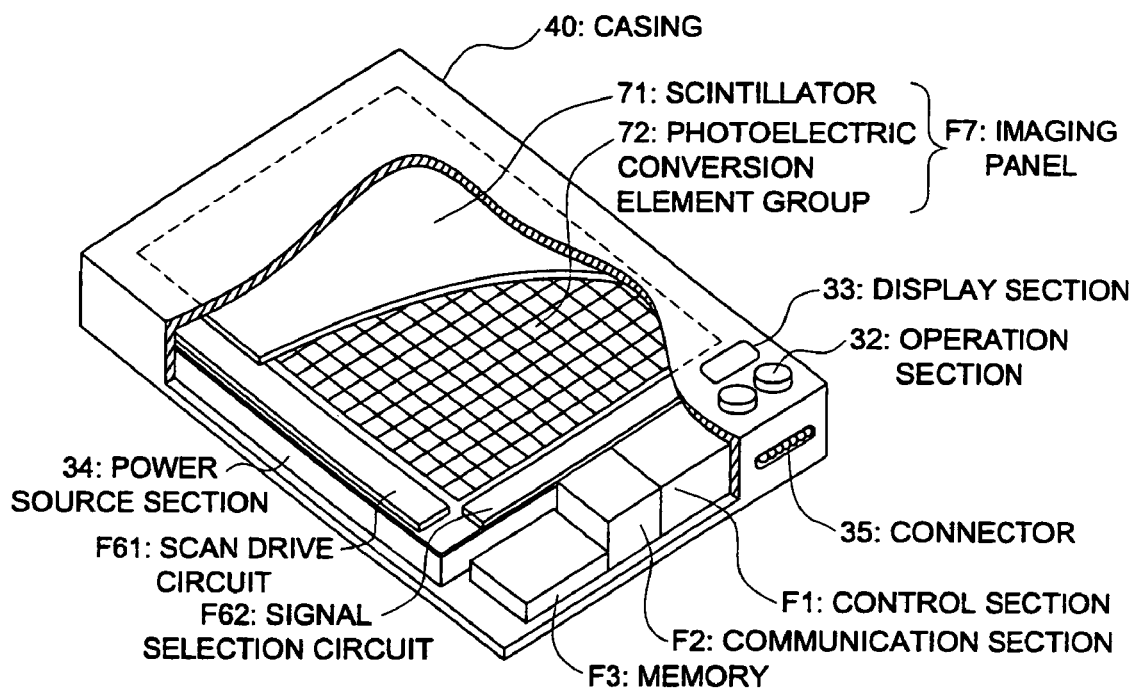
FIG. 2 is an external view of the radiation image detecting device F.

Referring to FIGS. 1 and 2, the following describes the radiation image detecting device F.

FIG. 2 is an external view of the radiation image detecting device F. The same components as those of FIG. 4 are assigned with the same reference numerals. The radiation image detecting device F is a portable radiographing apparatus, and is referred to as the so-called FPD (Flat Panel Detector). As illustrated, the radiation image detecting device F (hereinafter also referred to as "FPD") includes a control section F1, communication section F2, memory F3, signal control circuit F6 (F61, F62), and imaging panel F7.

The communication section F2 serving as a receiving section and transmission section performs wireless communication with the wireless access point 2 installed in the radiographing room. The wireless system is based on the wireless LAN system conforming to the IEEE802.11 Codes. Without being restricted thereto, it can be based on other waveform systems such as UWB (Ultra Wide Band) and Bluetooth, or optical system such as infrared communication.

The imaging panel F7 serving as a radiation image data acquisition section includes a scintillator 71 and a photoelectric conversion element group 72. The scintillator 71 emits visible light according to the amount of radiation coming from the radiation irradiation apparatus R6. The visible light having been emitted is converted into a digital image signal conforming to the amount of light by the photoelectric conversion element group 72. This digital image signal is read out and is stored temporarily in the memory F3. In this case, the photoelectric conversion element group 72 is made up of the two-dimensional array of a plurality of photoelectric conversion elements for conversion of light into electric signal for each pixel (also called the light receiving element or detecting element). One photoelectric conversion element corresponds to one pixel of the radiation image. These pixels are arranged over the entire size of the patient radiographed region at a density of 200 through 400 pixel/25.4 mm, for example.

A plurality of radiation images can be stored in the memory F3 according to the capacity. For example, the radiation image data corresponding to several images through several tens of images can be stored in the memory F3. Further, the radiographing reservation sent from the control terminal CS through the management server MS is also stored in the memory F3.

The control section F1 includes a CPU and system memory. By executing various forms of programs stored in the system memory by the CPU, the entire radiation image detecting device F is controlled. The control section F1 keeps constant control of the reception state of the radiation image detecting device F.

The power source section 34 made up of a battery supplies power to the entire radiation image detecting device F. After radiographing, by physically connecting with the connector 35, data communication (wired communication) of the irradiation apparatus R with the radiation image detecting device F is performed and the power source section 34 is charged.

The imaging panel F7 is connected with the scan drive circuit F61 that reads out the electrical energy stored in the photoelectric conversion element group 72 in conformity to the intensity of the radiation applied, and with the signal selection circuit F62 for outputting the stored electrical energy as the image signal. In this case, the scan drive circuit F61, signal selection circuit F62, control section F1, memory F3 and communication section F2 inside the casing 40 are covered with radiation shielding members (not illustrated) so as to avoid scattering of radiation inside the casing 40 and radiation being applied to each circuit.

In the present embodiment, the above description has referred to an indirect FPD for indirectly detecting the radiation using a scintillator. Without the present invention being restricted thereto, it is also possible to use a direct FPD wherein radiation is directly converted to electrical signal by the photoelectric conversion element.

[Control Terminal]

The control terminal CS (also called the console) is made up of a control section C1, communication section C2, memory C3, image processing section C4, and operation/display section C5. The operation/display section C5 includes a liquid crystal display section, a touch panel section arranged on top of the display section, mouse and keyboard. Various forms of radiographing order are inputted by operating the operation/display section C5, or are received from the management server (not illustrated) of the RIS or HIS connected to the communication line N or management server MS.

The image processing section C4 can process the radiation image data (also called the image data simply below) acquired by the radiation image detecting device F, thereby adjusting density gain or converting spatial frequency.

The memory C3 stores the radiographing order received from the management server MS over the communication line N and the radiation image data sent from the radiation image detecting device F, and also stores the radiographing order and image data, correlated with each other. The control terminal CS is assigned with the "control terminal ID" information unique to the control terminal CS to identify each control terminal CS, and is stored in the memory C3 in advance.

[Management Server]

The management server MS of FIG. 1(b) contains a control section M1, a communication section M2 that serve as a receiving section and memory M3. The database of the memory M3 contains the patient information, radiographing order information, the size that can be radiographed and memory capacity for each radiation image detecting device.

The control section M1 is made up of a CPU, system memory and others. The entire radiation image detecting device F is controlled as various forms of programs stored in the system memory are executed by the CPU. The control section M1 keeps constant control of the reception state of the radiation image detecting device F.

First Embodiment

Figure 3:
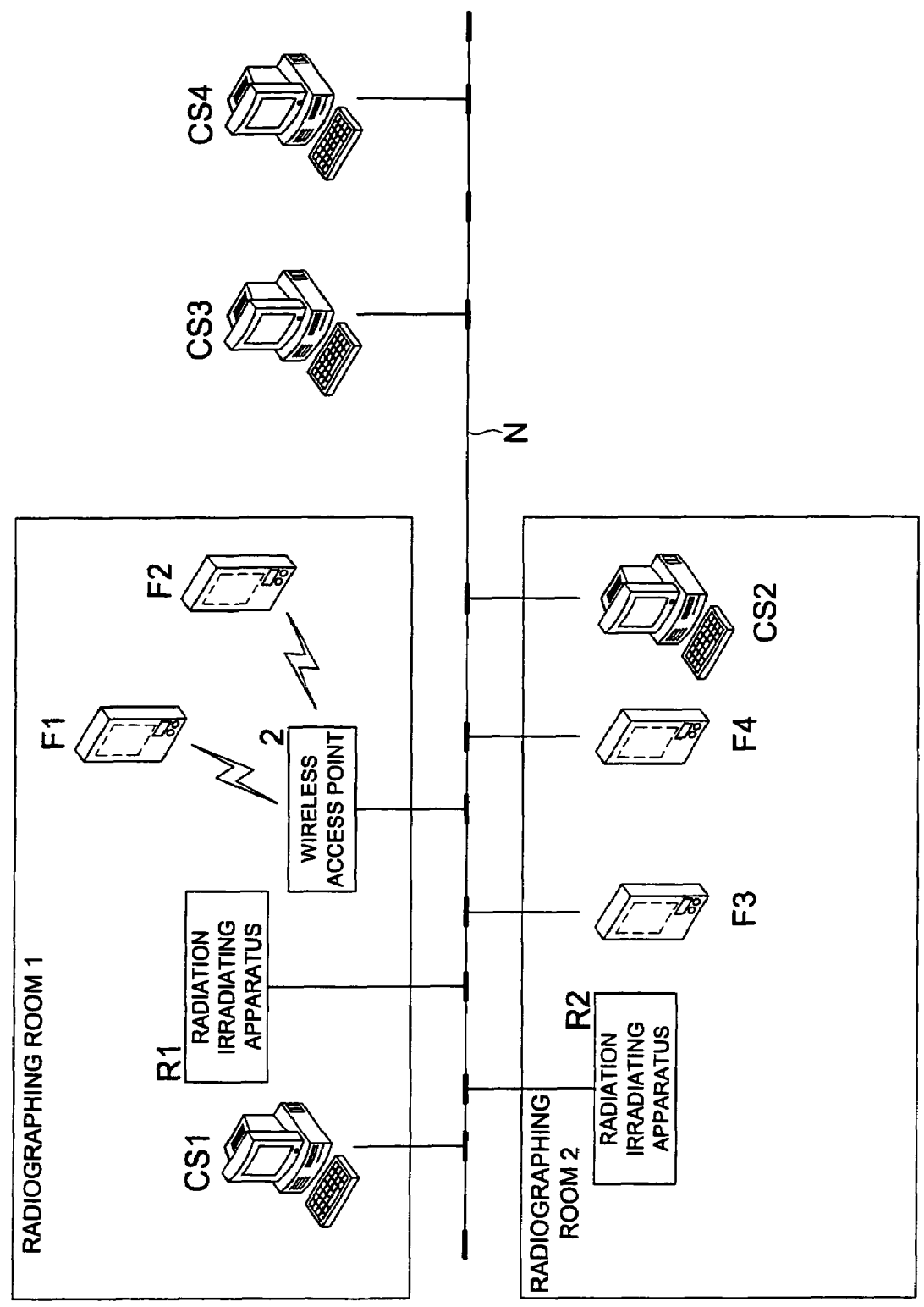
FIG. 3 is a schematic view representing the radiographing system in the embodiment.

FIG. 3 is a schematic view representing the radiographing system of the embodiment. As shown in FIG. 3, the radiographing system is connected with the irradiation apparatuses R1 and R2 shown in FIG. 1, a plurality of radiation image detecting devices F1 through F4 (hereinafter referred to as "FPD 1 through FPD 4" or "FPD" simply), and a plurality of control terminals CS1 through CS4 over one and the same communication line N. The FPD 1 and FPD 2 of the radiographing room 1 are connected with the communication line N by a wireless system, while the FPD 3 and FPD 4 of the radiographing room 2 are connected with the communication line N by a wired system through the connector 35 and cradle (not illustrated).

FIG. 4 is a diagram representing the control flow of the radiographing system in the embodiment. It shows the control flow of the operation between the control terminal CS and FPD performed by the operator such as a radiographing technician or doctor.

In the first place, in Step S0, a radiographing order to be executed by the irradiation apparatus R and FPD is selected from among a plurality of radiographing orders stored in the memory C3 of the control terminal CS.

FIG. 5 is a diagram showing an example of a plurality of radiographing orders stored in the memory C3 of the control terminal CS. As shown in FIG. 5, each radiographing order is assigned with a unique radiographing order ID (p1). Each radiographing order is assigned with the information on radiographing conditions such as a patient ID (p2), department of diagnosis (p6), radiographed region (p7) and radiographing direction (p8). Further, the patient ID (p2) is correlated with patient information such as a patient name (p3), sex (p4) and age (p5). Accordingly, such information is also assigned to each radiographing order. The patient information is intended to specify a patient, whereby confusion of patients is prevented. For example, the radiographing order ID "61201001" denotes that radiographing of the front A-P (irradiation from the front side to the back side) of the chest of Mr. Ichiro Suzuki bearing the patient ID "100085" is to be performed in the department of surgery.

The radiographing order list of FIG. 5 appears on the display screen of the operation/display section C5 of the control terminal CS. Thus, the technician selects the radiographing order ID (p1) to be used, from among the displayed radiographing orders. It should be noted that the radiographing order can be inputted directly from the operation/display section of the control terminal CS. Alternatively, it is also possible to receive the radiographing order registered in the radiation management server (not illustrated) or information system HIS in the hospital.

In Step S1, a request for radiographing reservation is sent to any one of the FPDs from the control terminal CS. In this case, the control terminal ID information of the relevant control terminal CS and the number of radiation images are also sent together.

In the FPD having received request for radiographing reservation, the control section F1 refers to the state of reception stored in the memory F3. If the current state is "Receiving" (Step S2: Yes), a reply is given to reject the reception of the radiographing reservation (Step S3). The control terminal CS having received the reply of rejection (Step S4), again follows the flow of Step S1 and thereafter in order to request reception of the radiographing reservation to FPDs other than the one wherein reception has been rejected.

The "Receiving" state starts at the time point when the radiographing reservation (to be described later) has been received from the control terminal CS, and terminates at the time point when all the radiation image data related to this radiographing reservation has been acquired or when the acquired radiation image data has been sent to the control terminal CS. The "Free" state is the reverse of the "Receiving" state. It starts from the time point of having acquired all the radiation image data related to radiographing reservation or from the time point of having sent the acquired radiation image data to the control terminal CS, to the time point of receiving the radiographing reservation from the control terminal CS. These states of reception are stored in the memory F3. Further, when the state of reception is "Receiving", the control terminal ID information of the control terminal CS having sent the received radiographing reservation, together with the state of reception and the number of radiation images, is stored in the memory F3. To be more specific, the control section F1 serves the functions of "radiographing reservation receiving section", "radiographing state control section" and "reception control section", while the memory F3 serves as the "storage section".

If the state of reception is not "Receiving" (Step S2: No), the control section F1 sets the FPD to the "Receiving" state, in other words, the "Receiving" state is stored in the memory F3 (Step S5). Further, the control terminal ID of the control terminal CS having sent the number of radiation images and radiographing reservation is stored in the memory F3 (Step S6), and a reply is sent to the control terminal CS having sent the radiographing reservation, notifying that radiographing reservation has been received (permission of reception) (Step S7). After that, other radiographing reservations are rejected until the "Receiving" state is cancelled.

In the control terminal CS, when the permission of reception is received, the radiographing order and the ID of the FPD having received the radiographing order are registered (Step S8), whereby the processing completes.

As described above, in the radiographing system wherein a plurality of control terminals and a plurality of FPDs are connected to one and the same communication line, in the "Receiving" state wherein radiographing reservation has been received from one control terminal apparatus, other radiographing reservations are rejected thereafter. This arrangement provides a radiographing system and a radiation image detecting device capable of avoiding repeated registration of one FPD from a plurality of control terminals, and hence preventing confusion of the radiation images for the patients.

In the present embodiment, radiographing reservation, the number of radiation images and control terminal ID are sent from the control terminal CS to the FPD, and the radiographing state, the number of radiation images and control terminal ID are stored in the memory F3 of the FPD. It is also possible to arrange such a configuration that the radiographing order including the information on the patient ID and radiographed region is sent from the control terminal CS, and the radiographing order having been sent is stored in the memory F3. This arrangement allows the radiographing order to be displayed on the display section 33 of the FPD, and permits the technician to check the radiographing order immediately before radiographing, whereby the confusion of the radiation images for the same patient can be prevented.

Figure 6:
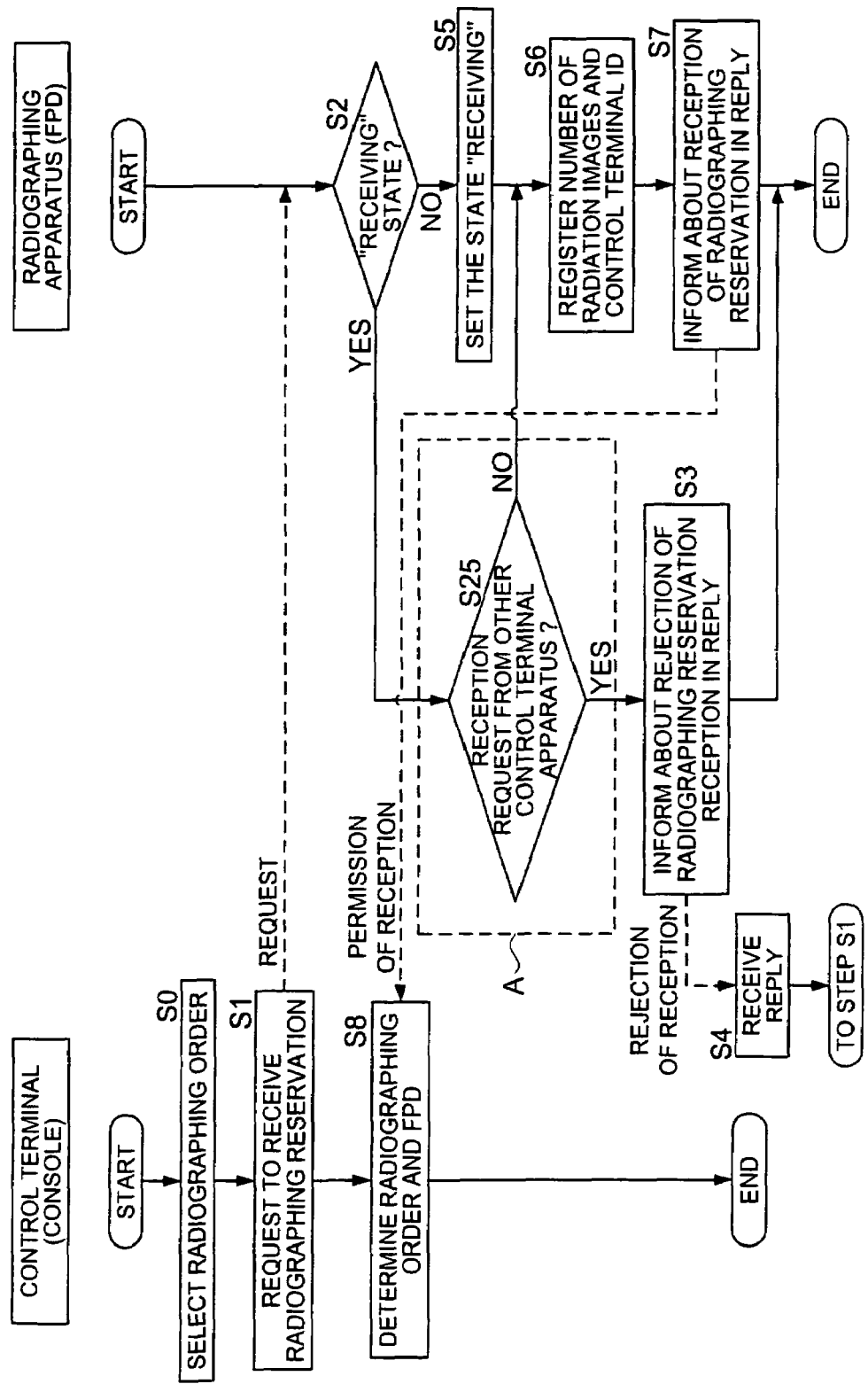
FIG. 6 is a diagram representing the control flow of the radiographing system in another embodiment.

FIG. 6 is a diagram representing the control flow of the radiographing system in another embodiment. The flow of FIG. 6 is formed by adding the flow enclosed in the broken line box A, to the flow of FIG. 4. Otherwise, FIG. 6 is the same as FIG. 4 and the description is omitted.

As shown in FIG. 6, despite the "Receiving" state (Step S2: Yes) at the time of requesting the radiographing reservation, if the radiographing reservation is not the one coming from other control terminal (Step S25: No), in other words, if there is agreement between the control terminal ID registered together with the radiographing state "Receiving" in the memory F3, and the control terminal ID having been sent together with the sent radiographing reservation, reception of the radiographing reservation is permitted. In this case, when the number of radiation images is registered, the current number of radiation images is added.

As described above, when radiographing reservation is to be registered from one control terminal CS, a plurality of radiographing reservations can be registered in the FPD. This has an advantage of enhancing the radiographing efficiency. Under this condition, one technician uses one control terminal CS to request radiographing reservations on a continuous basis, wherein a plurality of radiographing operations are performed for one and the same patient. In few cases, radiographing orders for different patients may be selected. In such cases, the technician is aware that a plurality of patients will be radiographed continuously. This arrangement does not easily allow confusion of patients to be caused by registration of overlapped radiographing reservations in one FPD.

Figure 7:
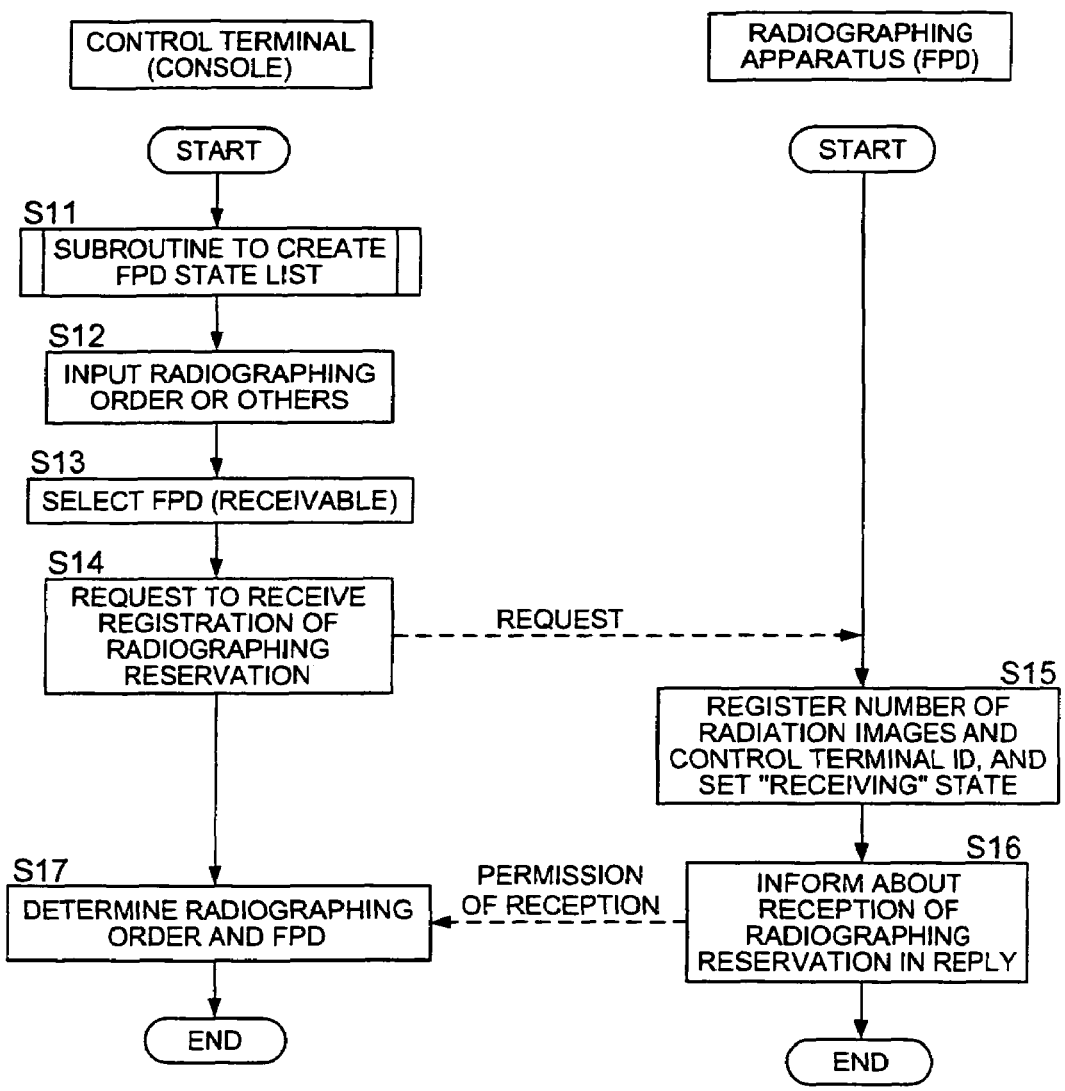
FIG. 7 is a diagram representing the control flow of the radiographing system in a further embodiment.

FIG. 7 is a diagram representing the control flow of the radiographing system in a further embodiment. In the flow in FIG. 7, it is intended to correctly identify the state of the FPD connected to the communication line N in advance. In the first place, the subroutine process of creating the FPD state list is applied in the control terminal CS (Step S11).

FIG. 8 is a diagram representing the subroutine processing for creating an FPD state list shown in Step S11 of FIG. 7. In Step S111, an inquiry about the state of reception is sent to all the FPDs connected to the communication line N.

If the FPD to which reference has been made in the next Step S112 is in the "Receiving" state (Step S113: Yes), the control section F1 of the FPD sends a reply notifying that the state is "Receiving", and also sends the "control terminal ID" stored together with the radiographing state "Receiving" through the communication section F2 (Step S114). In the meantime, if the state is not "Receiving" (Step S113: No), the control section F1 of the FPD sends a reply notifying that the state is not "Receiving" (Step S115). Upon completion of receiving the replies from all the FPDs connected to the communication line N (Step S116: Yes), the control terminal CS creates the state list of each FPD (Step S117), whereby processing terminates. FIG. 9 shows an example of the state list. Together with the ID number (a1) of each FPD, the state of reception (a2) and the control terminal ID (a3) that is stored together with the state of reception are displayed in the list. The ID number of the FPD is a unique ID number for identification, and is assigned to each FPD in advance.

Going back to the flow of FIG. 7, the Step S11 is followed by the step of inputting the radiographing order (Step S12), then by the step of selecting the FPD (Step S13). Referring to the drawing, the following describes the operation procedure of selecting the FPD.

Figure 10:
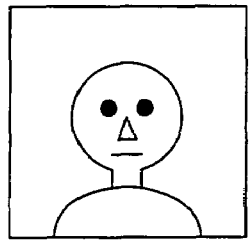
FIG. 10 is a detailed diagram representing the operation screen of the operation/display section C5 in the control terminal CS.

FIG. 10 is a detailed diagram representing the operation screen of the operation/display section C5 in the control terminal CS. As shown in FIG. 10, the selected radiographing order information appears in the display column D2, and the display column D1 shows the state list of the FPD that can be selected. This state list is obtained in Step S11. In the example shown in this drawing, the aforementioned example of FIG. 9 is represented. The display column D3 shows the ID number of the control terminal being operated.

In this drawing, on the FPD lists appearing on the display column D1, the FPD in the "Receiving" state rejects reception of radiographing reservation (radiographing order) from other control terminal apparatuses, and therefore, "B" appears in the "Receivable or Not" column D101 notifying rejection of reception (D101a). In the illustrated example, FPD 04 shown in the D14 signifies that there is agreement between the registered "CS02" of the control terminal ID (D102) and the CS02 (D3 column) of the control terminal ID being operated, despite the "Receiving" state, and the condition of "from other control terminal apparatuses (Step S25 in FIG. 6)" is not satisfied; thus, "A" is shown in the "Receivable or Not" column notifying that the reservation can be received. The column D103 of the "Location" in the D1 column indicates the particular location of each FPD in the connection with the communication line N.

In the radiographing apparatus selection screen, after the FPD for radiographing reservation (e.g. FPD 03) has been selected, the selection button D4 of FIG. 8 is pressed. Then a request for receiving the radiographing order together with the control terminal ID "CS02" is sent to the FPD having been selected (Step S14). The FPD having been requested registers the number of radiation images and control terminal ID, and sets the "Receiving" state (Step S15). A reply is sent to the control terminal CS whose request has been received to notify reception of radiographing reservation (Step S16). Radiographing reservation and FPD ID are determined in the control terminal (Step S17), whereby processing terminates.

In the example of the embodiment, the control terminal ID and FPD ID are assigned with unique control numbers. It is also possible to use the IP address or MAC address for connection with the communication line.

As described above, in a radiographing system wherein a plurality of control terminals and a plurality of FPDs can be connected over one and the same communication line, subsequent reception of other radiographing reservations is rejected in the "Receiving" state wherein radiographing reservation has been received from one control terminal apparatus. This arrangement provides a radiographing system and radiation image detecting device capable of avoiding overlapped registration in one FPD from a plurality of control terminals, and hence preventing confusion of the radiation images for the patients.

[Control to Cancel the "Receiving" State]

Figure 11:
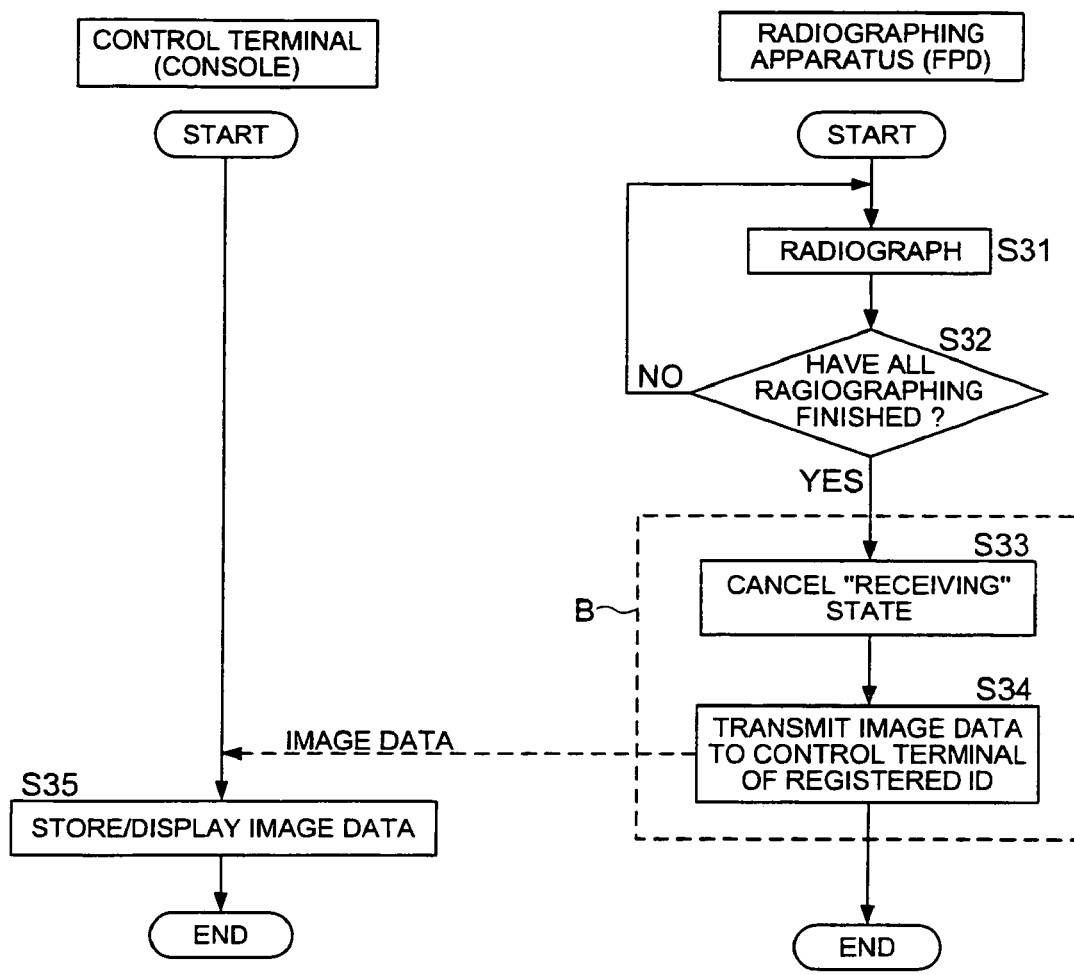
FIG. 11 is a diagram showing the control flow of the radiographing system in a still further embodiment.

FIG. 11 is a diagram showing the control flow of the radiographing system in a further embodiment. In the flow shown in FIG. 11, it is intended to cancel the "Receiving" state upon completion of the step of radiographing. It shows the control flow following those of FIG. 4, FIG. 6 and FIG. 7.

The subject to be examined (patient) 100 is radiographed according to the radiographing order (Step S31). The term "radiographing" in the sense in which it is used here refers to the step of applying the radiation from the irradiation apparatus R to the subject 100, and storing the radiation image data into the memory F3 of the FPD based on the amount of radiation having passed through the subject.

The step of radiographing is continued based on the radiographing reservation. Upon completion of radiographing for all radiographing reservations (for the number of radiation images) (Step S32: Yes), the "Receiving" state of the FPD is cancelled (Step S33). Upon completion of cancellation, the subsequent registration of the radiographing reservation from other control terminal CS can be received. In the control section F1, the number of radiation images is counted. The number of radiation images registered (in Step S6 of FIG. 4, etc.) is subtracted by the number equivalent to the number of radiographing operations. When the remaining number of radiation images has been reduced to zero, all radiographing operations are determined to have terminated.

The FPD sends the radiation image data obtained by radiographing, to the control terminal CS of the registered control terminal ID ((CS02) in the example of FIG. 10) (Step S34). In the control terminal CS, image data having been received is stored in the memory C3, and is processed by the image processing section C4 as required. After that, the radiation image is displayed on the display screen of the operation/display section (Step S35), whereby processing terminates.

Figure 12:
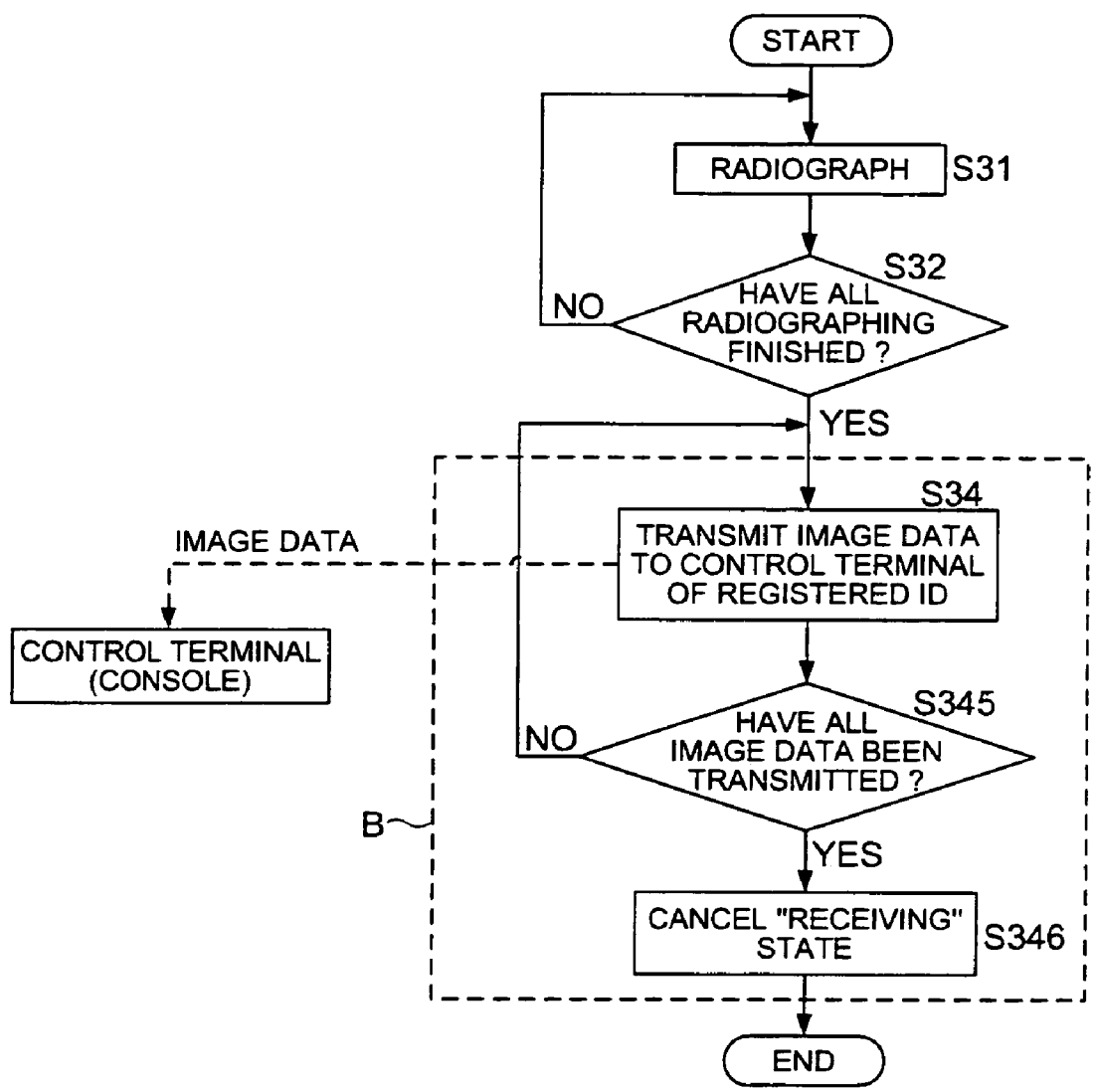
FIG. 12 is a diagram representing the control flow of a variation of FIG. 11.

FIG. 12 is a diagram representing the control flow of a variation of FIG. 11. In the flow shown in FIG. 12, the "Receiving" state is cancelled upon completion of transmission of the image data. The control flow is the same as that of FIG. 11 except that the broken line box B of FIG. 11 is modified and the description is omitted.

In Step S34, radiation image data is sent to the control terminal CS of the control terminal ID registered. Upon completion of transmission of all the radiation image data obtained by radiographing (Step S345), the "Receiving" state of the FPD is cancelled (Step S346), whereby processing terminates.

As described above, upon completion of radiographing reservation having been registered, the "Receiving" state of the FPD is cancelled. Then subsequent reception of other radiographing reservations from other control terminal CSs becomes possible. Thus, in a radiographing system wherein a plurality of control terminals and a plurality of FPDs are connected over one and the same communication line, this arrangement provides a radiographing system and radiation image detecting device capable of avoiding overlapped registration in one FPD from a plurality of control terminals, and hence preventing confusion of the radiation images for the patients, thereby ensuring effective use of the FPD.

Second Embodiment

Figure 13:
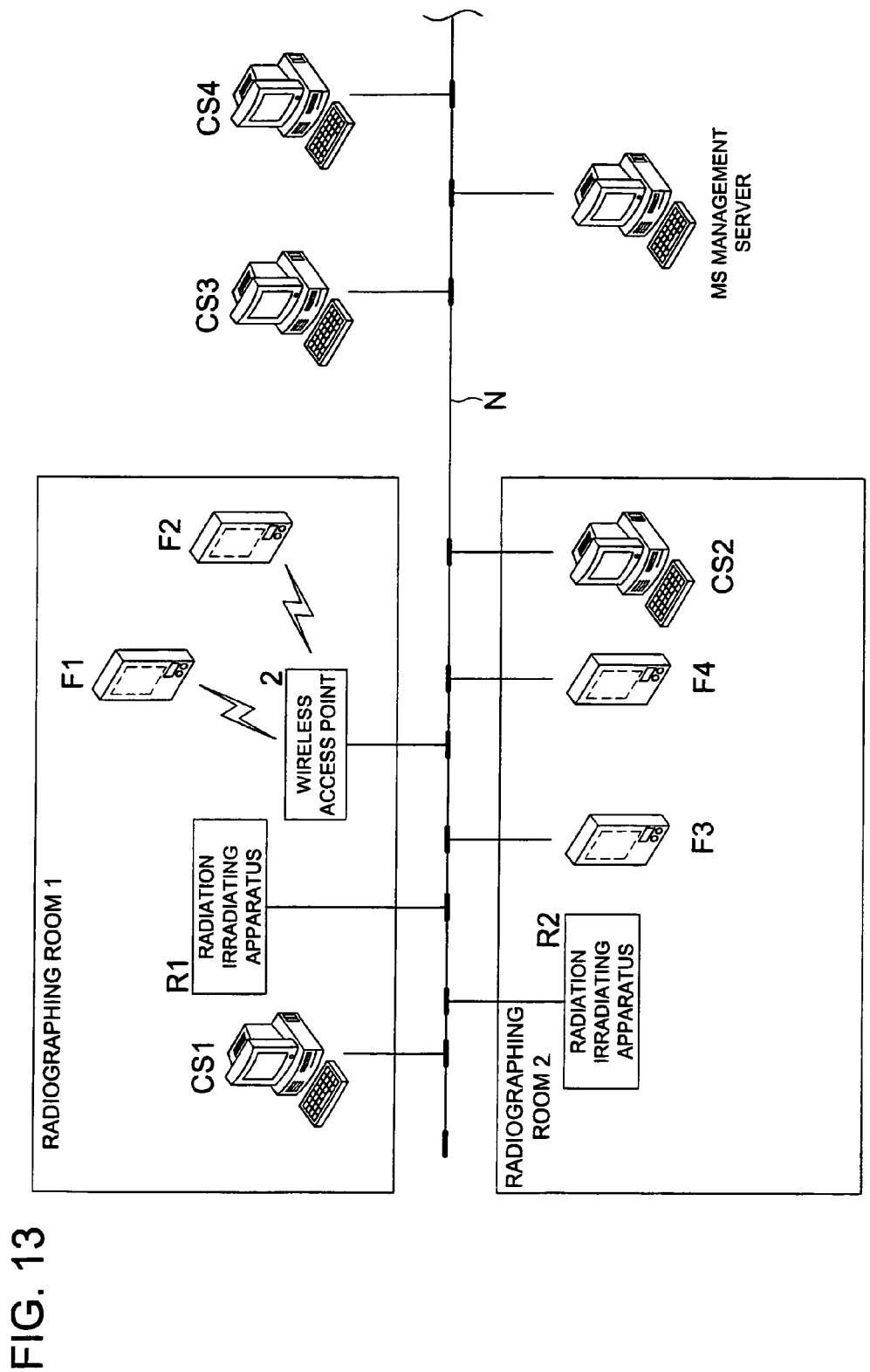
FIG. 13 is a schematic view representing the radiographing system in the embodiment.

FIG. 13 is a schematic view representing the radiographing system in the second embodiment. As shown in FIG. 13, the radiographing system is connected with a plurality of irradiation apparatuses R1 and R2; a plurality of radiation image detecting devices F1 through F4 (hereinafter referred to as "FPD 1 through FPD 4" or "FPD"); a plurality of control terminals CS1 through CS4; and management server MS over one and the same communication line N. The FPD 1 and FPD 2 of the radiation room 1 are connected with the communication line N through wireless system. The FPD 3 and FPD 4 of the radiographing room 2 are connected with the communication line N through wired system with using the connector 35 or cradle (not illustrated).

It should be noted that each control terminal CS and each radiation image detecting device F are provided with the control terminal ID and FPD ID (detecting device ID) as a unique ID number for the purpose of identification.

Figure 14:
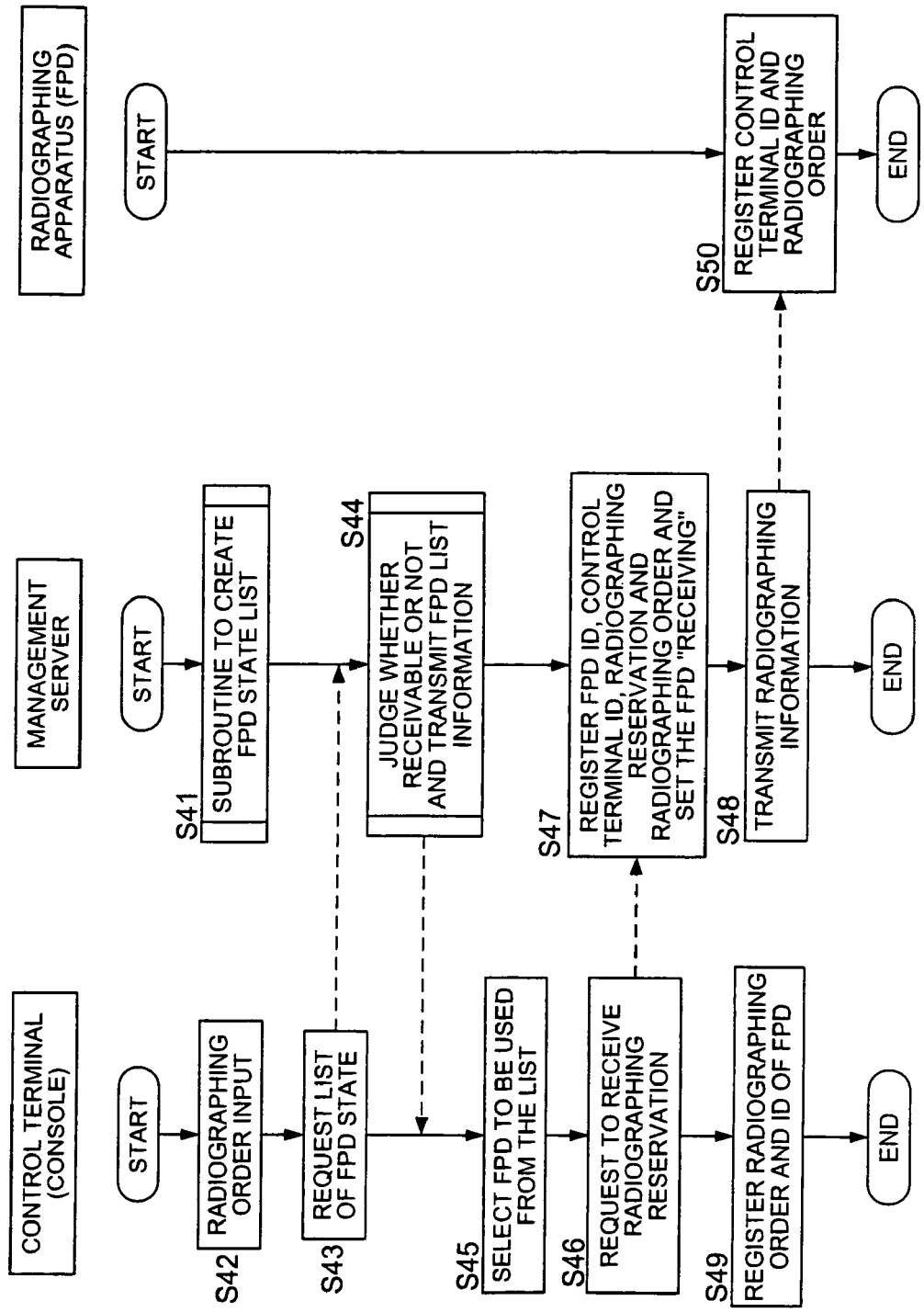
FIG. 14 is a diagram representing the control flow of the radiographing system in the embodiment.

FIG. 14 is a diagram representing the control flow of the radiographing system in the embodiment. It shows a control flow for the FPD, management server and control terminal CS operated by the operator (radiographing technician). In the first place, the management server MS executes subroutine processing to create an FPD state list (Step S41).

Figure 15:
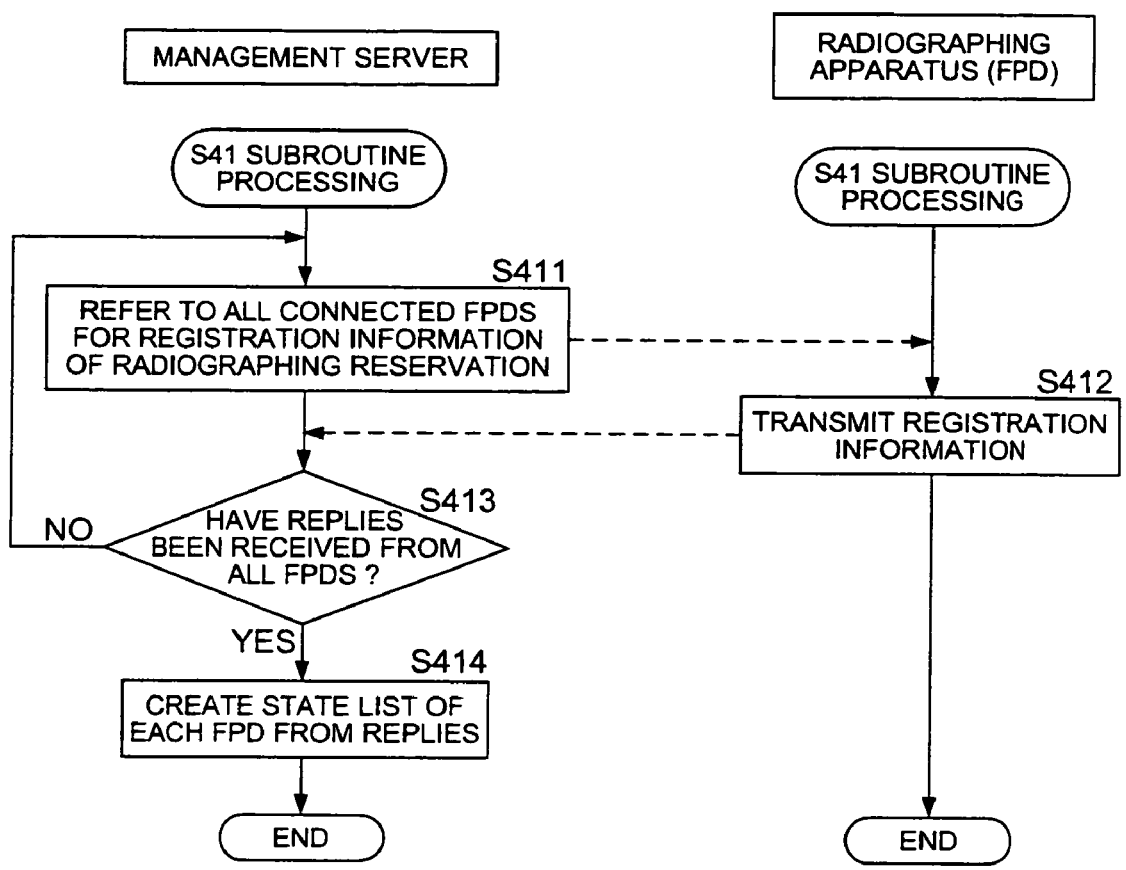
FIG. 15 is a diagram representing the subroutine processing for creating an FPD state list.

FIG. 15 is a diagram representing the subroutine processing for creating an FPD state list shown in Step S41 of FIG. 14. In Step S411 of FIG. 15, an inquiry about information on the registration of radiographing reservation is sent by the control section M1 of the management server to all the FPDs connected to the communication line N.

In respect to the inquiry, each FPD sends registration information (Step S412). The registration includes the radiographing reservation stored in the memory F3 and the control terminal ID of the control terminal whose radiographing reservation has been received.

Upon receipt of replies from all the FPD connected (Step. S413: Yes), the control section M1 of the management server creates a state list of each FPD based on the received replies (Step S414), whereby processing terminates.

FIG. 9 is a diagram representing an example of the FPD state list created in Steps S414. The FPD identification ID (a1) as a detecting device ID, state of reception (a2) and control terminal ID (a3) are formed into lists. It should be noted that the control terminal ID and detecting device ID are stored in the memory M3, correlated with each other.

Going back to the control flow of FIG. 14. In the control terminal CS, the radiographing order is inputted by the operation/display section C5 (Step S42). Instead of inputting from the operation/display section C5, it is also possible to arrange such a configuration that the control section C1 acquires the radiographing order stored in the management server MS connected to the communication line N and the technician selects a desired radiographing order from among the radiographing orders listed displayed on the operation/display section C5.

FIG. 5 is a diagram showing an example of a plurality of radiographing orders stored in the memory M3 of the management server MS. As shown in FIG. 5, each radiographing order is assigned with a unique radiographing order ID (p1), which includes the information on the radiographing conditions as exemplified by patient ID (p2), department of diagnosis (p6), radiographed region (p7) and radiographing direction (p8). Further, the patient ID (p2) is correlated with patient information such as patient name (p3), sex (p4) and age (p5). Accordingly, the patient information is also stored together. Patient information is intended to specify a patient. This eliminates the possibility of confusion with another patient. For example, the radiographing order ID "61201001" denotes that the front A-P (irradiation from the front side to the back side) of the chest of Ichiro Suzuki bearing the patient ID "100085" is to be radiographed in the department of surgery.

This is followed by the Step S43 wherein the control section C1 of the control terminal CS sends an inquiry to the management server MS about the FPD connected to the communication line N and the state list of them. In this case, the control terminal ID previously assigned to the control terminal CS is sent. The management server attaches the information on the result of the control section M1 determining the approval or rejection of reception of each FPD to the FPD list information and sends it (Step S44). Referring to the drawing, the following describes the information on the result of determining the approval or rejection of reception, prior to description for subroutine processing in Steps S44.

FIG. 10 is a detailed diagram representing the operation screen of the operation/display section C5 in the control terminal CS. As shown in FIG. 10, the display column D2 shows the radiographing order information inputted or selected in Step S42, and the display column D1 shows the state list of the FPD which is created in Steps S41 by the management server MS and which is sent to the control terminal CS after "Receivable or Not" has been determined in Step S44. Further, the display column D3 also shows the control terminal ID for identification of the control terminal apparatus being operated.

"Receivable" and "Not Receivable" given in the row D101 (Receivable or Not) of the display column D1 in FIG. 10 represent information of the decision on the permission or rejection of reception. The following describes the control flow for this decision.

[Subroutine Processing for Permission or Rejection of Reception]

Figure 16:
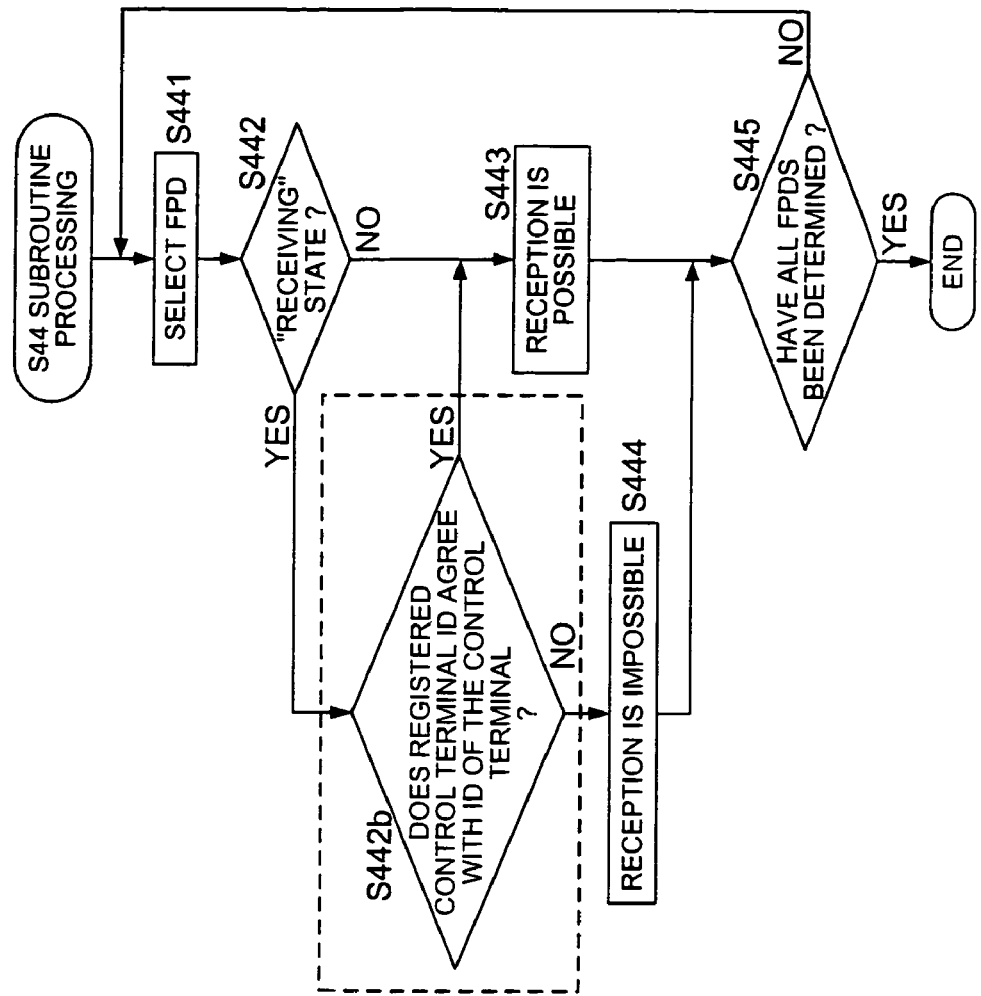
FIGS. 16(*a*) and (*b*) are diagrams representing the subroutine processing in S14.
Figure 16:
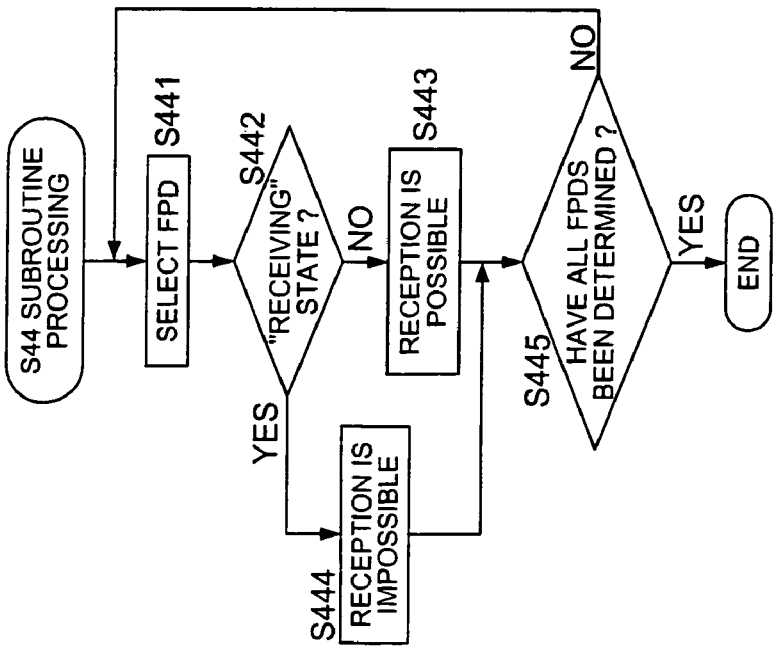

FIGS. 16(a) and 16(b) are diagrams representing the subroutine processing in Steps S44 of FIG. 14. FIG. 16(a) shows an example.

In Steps S441 of FIG. 16(a), the control section M1 of the management server MS selects one FPD connected to the communication line N, out of the FPDs, for example, FPDs 1 through 4. The control section M1 refers to the state list created in Step S414. If the state of reception (a2 of FIG. 9) of the FPD selected in Steps S441 is "Receiving" (Step S442: Yes), the "Receivable or Not" is set to "Not Receivable" (Step S444). If the state is not "Receiving", namely, "Free" (Step S442: No), the "Receivable or Not" is set to "Receivable" (Step S443). In other words, "Receivable or Not" D101 of FIG. 10 is set to "Receivable". This procedure is repeated until decision is made for all the FPDs (Step S445).

The "Receiving" state starts at the time point when the radiographing reservation (to be described later) has been received by the management server MS from the control terminal CS, and terminates at the time point when (the management server MS has received the information that) all the radiation image data related to this radiographing reservation has been acquired by the radiation image detecting device F or when (the management server MS has received the information that) the acquired radiation image data has been sent to the control terminal CS. The "Free" state is the reverse of the "Receiving" state. It starts from the time point when (the management server MS has received the information that) all the radiation image data related to radiographing reservation has been received or from the time point when (the management server MS has received the information that) the received radiation image data has been sent to the control terminal CS, to the time point of receiving the radiographing reservation from the control terminal CS. These states of reception are stored in the memory M3. Further, when the state of reception is "Receiving", the control terminal ID information of the control terminal CS having sent the received radiographing reservation, together with the state of reception, is stored to the memory M3. To be more specific, the control section M1 serves the functions of "radiographing reservation receiving section", radiographing state control section and reception control section, while the memory M3 serves as the storage section.

As described above, when the radiation image detecting device F is in the state of "Receiving" and has received radiographing reservation from one control terminal apparatus CS, the "Receivable or Not" is set to "Not Receivable" in the management server MS. After that, the management server MS ensures that other radiographing reservation for this radiation image detecting device is not received. This arrangement eliminates the possibility of overlapped registration of the radiographing reservation in one radiation image detecting device F.

FIG. 16(b) is a variation of FIG. 16(a). The same reference numerals are assigned to the same processing items. In the variation of FIG. 16(b), even if the state list (a2 of FIG. 9) is in the state of "Receiving" (Step S442: Yes), the "Receivable or Not" is set to "Receivable" (Step S443), if there is agreement in the state list between the control terminal ID registered (stored) in the memory M3 (a3 of FIG. 9) and control terminal ID having been sent in Step S43 (Step S442b: Yes). Radiographing reservation is permitted for the radiation image detecting device F corresponding to the detecting device ID (ID of the FPD) correlated with the control terminal ID.

As described above, in the case of radiographing reservation from one and the same control terminal CS, a plurality of radiographing reservations for this radiation image detecting device F are permitted. Accordingly, after completion of one radiographing operation, the technician is allowed to continue radiographing operations without having to perform the next radiographing reservation from the control terminal CS. This arrangement provides an advantage of effective radiographing. Further, under such circumstances, one technician performs radiographing reservation on a continuous basis using one control terminal CS. In almost all cases, the technician performs a plurality of radiographing operations for one and the same patient. Only on rare occasions, the radiographing order of a different patient may be selected. In such cases, the technician is aware that a plurality of patients are radiographed on a continuous basis. Thus, confusion of images due to overlapped registration of radiographing reservation in one FPD does not occur easily.

Going back to the flow of FIG. 14, the FPD for radiographing is selected from the list in Step S45. The following describes the method of this selection with reference to the display screen of FIG. 10.

In FIG. 10, in the FPD list displayed in the display column D1, the FPD in the state of "Receiving" in the state column D17 does not receive any radiographing order from other control terminal apparatuses. Accordingly, the "Receivable or Not" column D101 is marked with "Not Receivable" to show that the order cannot be received (D101a). In the example of this drawing, the FPD 04 of the D14 is in the state of "Receiving" in the state column D17. However, according to the control flow of FIG. 16(b), the "CS02" of the control terminal ID (D102) registered together with the radiographing reservation agrees with the CS02 (D3 column) of the ID of the control terminal being operated, and therefore, this does not meet the condition of receiving order from other control terminal apparatuses (Step S442b of FIG. 16(a)). Thus, the "Receivable or Not" column D101 is marked with "Receivable", indicating that the order can be received (D101b). The "Location" column D103 in the D1 column shows the location where each FPD is present. To put it more specifically, it shows the location connected with the communication line N.

In Step S45, an FPD for radiographing is selected from the receivable FPD list (FPD 03 in the example of FIG. 9), and the selection button D4 is pressed, and then selection of the FPD terminates. The control section C1 of the control terminal CS sends the radiographing reservation and radiographing order for this radiographing reservation as well as the control terminal ID to the management server MS (Step S46). The management server MS registers the FPD ID, control terminal ID, radiographing reservation and radiographing order having been sent in Step S46, and sets the state of the relevant FPD (e.g. FPD 03) to "Receiving" (Step S47).

The control section M1 of the management server MS notifies the relevant FPD (e.g. FPD 03) of the fact that the control terminal ID, radiographing reservation, radiographing order and radiographing reservation have been registered as the information on radiographing received in Step S47 (Step S48). The FPD received this information registers it in the memory F3 (Step S50), whereby processing terminates.

In the example of the present embodiment, the control terminal ID and FPD ID are assigned with unique control numbers. It is also possible to use the IP address or MAC address to be used at the time of connection to the communication line.

As described above, in a radiographing system wherein the management server MS, a plurality of control terminals CS and a plurality of FPDs can be connected over one and the same communication line, when the FPD is in the state of "Receiving" of having received radiographing reservation from one control terminal apparatus, the management server MS ensures that any other radiographing reservation for this FPD is not received. This arrangement provides a radiation system capable of avoiding overlapped reservation in one FPD from a plurality of control terminals, and hence preventing confusion of the radiation images for the patients.

[Control to Cancel "Receiving" State]

Figure 17:
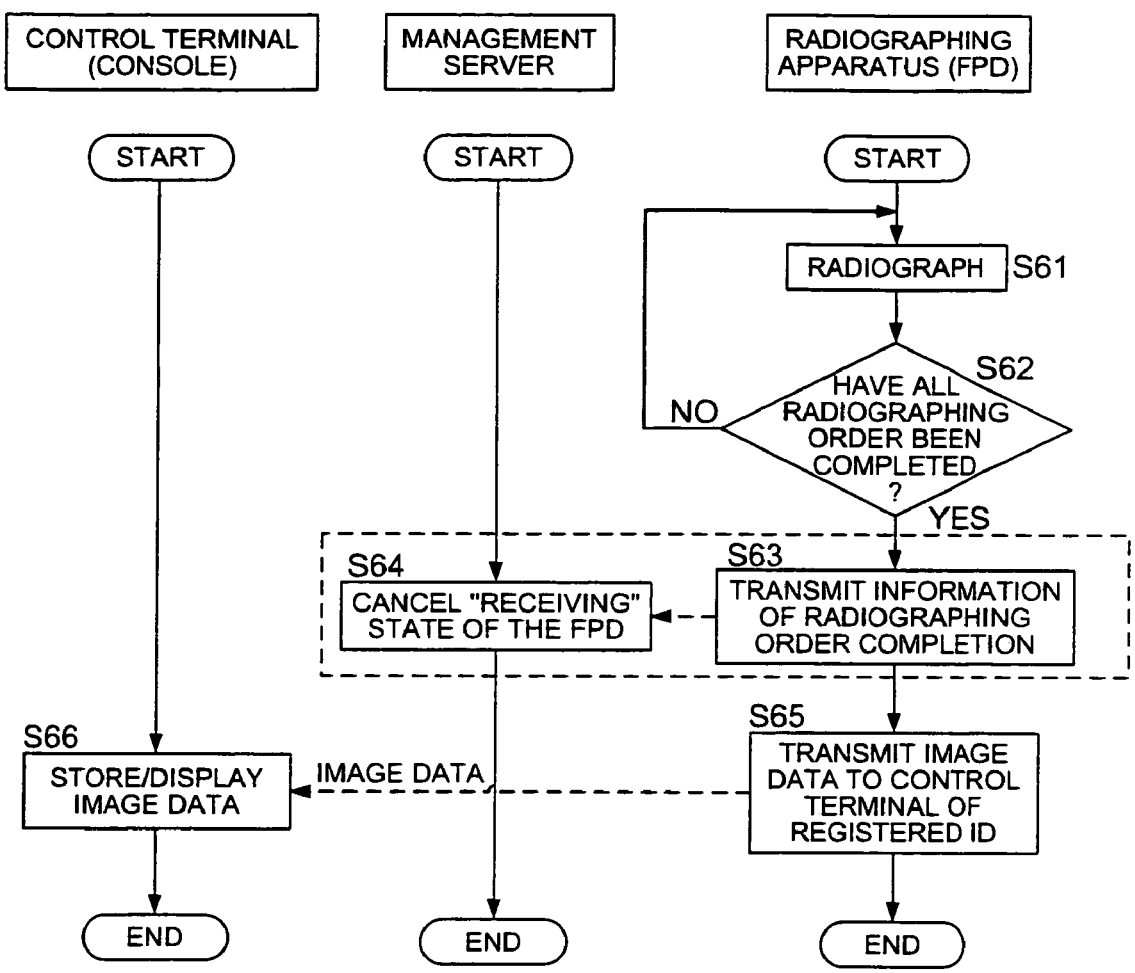
FIG. 17 is a diagram representing the control flow of the radiographing system in still further embodiment.

FIG. 17 is a diagram representing the control flow of the radiographing system in still further embodiment. The flow of FIG. 17 shows that the "Receiving" state is cancelled upon completion of the radiographing. It follows the flow of FIG. 14.

In the first place, in the Step S61 the FPD is used to radiograph the subject to be examined (patient) 100 based on the radiographing order registered in Steps S50. The term "radiographing" in the sense in which it is used here refers to the step of applying the radiation from the irradiation apparatus R to the subject 100, and storing the radiation image data into the memory F3 of the FPD based on the amount of radiation having passed through the subject.

When there are a plurality of radiographing orders, the FPD continues to be used for radiographing operations. Upon completion of radiographing of all radiographing orders (Step S62: Yes), a signal indicating the completion of the radiographing order together with the FPD ID is sent to the management server MS (Step S63). Having received the signal notifying the completion of radiographing orders, the management server MS cancels the "Receiving" state of the FPD (e.g. FPD 03) corresponding to the FPD ID sent in Steps S63 in the state list created in Steps S41 (Step S64). Cancellation of the "Receiving" state allows the FPD 03 to receive registration of the radiographing reservation from other control terminal CSs.

The FPD sends the radiation image data obtained by radiographing, together with its own FPD ID, to the control terminal CS assigned with the control terminal ID registered in Step S50 (Step S65). In the control terminal CS, the radiation image data sent in Steps S65 is stored in the memory C3, and is processed as required by the image processing section C4. After that, radiation image is displayed on the display screen of the operation/display section C5 (Step S66), whereby processing terminates.

Figure 18:
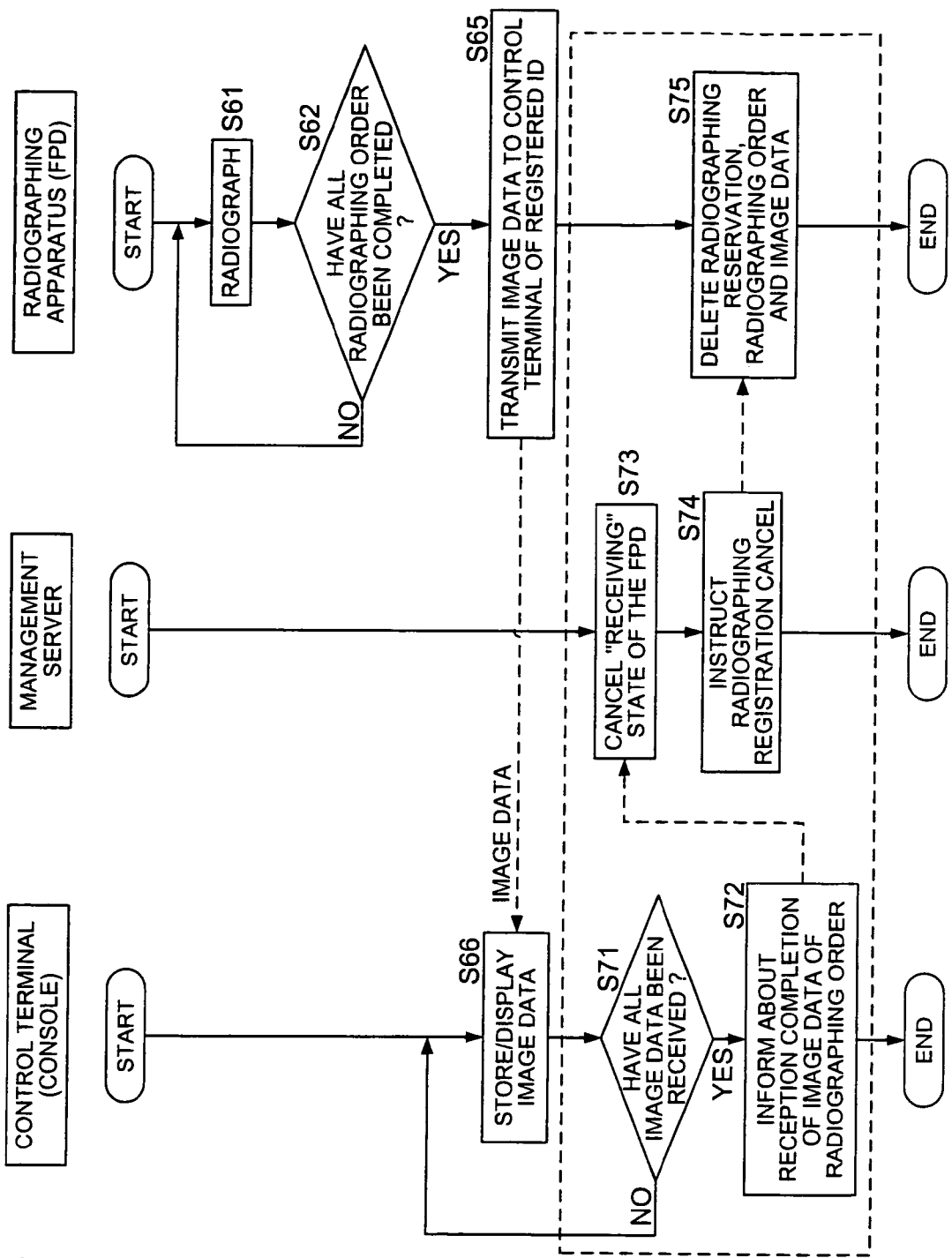
FIG. 18 is a diagram representing the control flow of a variation of FIG. 10.

FIG. 18 is a diagram representing the control flow of a variation of FIG. 17. The flow of FIG. 18 shows that the "Receiving" state is cancelled after completing transmission of the image data. The control flow of FIG. 18 is the same as that of FIG. 17 except that the portion inside the broken line box is modified, and will not be described to avoid duplication.

The FPD sends the radiation image data to the control terminal CS assigned with the control terminal ID registered in Step S50 (FIG. 14). When the control terminal CS has completed reception of all the radiation image data (Step S71: Yes), the information that the image data related to the registered radiographing order has been received, together with the FPD ID received in Step S65, is sent to the management server MS (Step S72). This arrangement allows the management server MS to cancel the "Receiving" state of the FPD corresponding to the FPD ID sent in Step S72 (Step S73). Further, an instruction is given to this FPD to cancel the radiographing reservation (Step S74).

The FPD receives the instruction to cancel the radiographing reservation sent in Step S74, and deletes the radiographing reservation, radiographing order and radiation image data having been stored in the memory F3 (Step S75).

As described above, upon completion of the radiographing order having been registered, the "Receiving" state of the FPD is cancelled. This procedure permits subsequent reception of the radiographing order from other control terminals CS. In a radiographing system wherein a plurality of control terminals and a plurality of FPDs are connected over one and the same communication line, this arrangement provides a radiographing system capable of avoiding overlapped registration in one FPD from a plurality of control terminals, and hence preventing confusion of radiation images of the patients, whereby effective use of the FPD is ensured.

In the present invention, in a radiographing system wherein a plurality of control terminals and a plurality of FPDs are connected over one and the same network, management is made to ensure that overlapped registration of radiographing reservations for different patients in one FPD from a plurality of control terminals. This arrangement provides a radiographing system and radiation image detecting device capable of preventing confusion of the radiation images of patients.

What is claimed is:

1. A radiographing system comprising:
   a control terminal apparatus for transmitting a radiographing reservation;
   a radiation image detecting device for obtaining radiation image data based on a radiation having passed through a subject, the radiation image detecting device being connected with the control terminal apparatus through a communication line;
   a radiographing reservation receiving section for receiving the radiographing reservation for the radiation image detecting device;
   a radiographing condition control section for setting a reception state of the radiation image detecting device to be a state of receiving when the radiographing reservation receiving section receives the radiographing reservation;
   a reception control section for prohibiting reception of another radiographing reservation for the radiation image detecting device related to a radiographing reservation which the radiation reservation receiving section has received when the reception state is the state of receiving.

2. The radiographing system of claim 1, further comprising:
   a receiving section for receiving a radiographing reservation and a control terminal ID for identifying a control terminal apparatus having transmitted the radiographing reservation;
   a storage section for storing a control terminal ID for identifying the control terminal apparatus having transmitted the radiographing reservation which the radiographing reservation receiving section has received and a detecting device ID for identifying the radiation image detecting device related to the radiographing reservation which the radiographing reservation receiving section has received, the control terminal ID and the detecting device ID being correlated with each other,
   wherein when the control terminal ID which the receiving section has received agrees with the control terminal ID stored in the storage section, the reception control section allows to receive the another radiographing reservation for the radiation image detecting device, which the receiving section has received, the radiation image detecting device corresponding to the detecting device ID correlated with the control terminal ID.

3. The radiographing system of claim 1,
   wherein the radiographing condition control section cancels the reception state of receiving of the radiation image detecting device after the radiation image detecting device acquires the radiation image data.

4. The radiographing system of claim 1,
   wherein the radiation image detecting device comprising;
   a transmission section for transmitting radiation image data, and
   wherein the radiographing condition control section cancels the reception state of receiving of the radiation image detecting device after the transmission section of the radiation image detecting device transmits the radiation image data.

5. The radiographing system of claim 1, comprising:
   a plurality of radiation image detecting devices;
   the control terminal apparatus for selecting a radiation image detecting device to be used among the plurality of radiation image detecting devices,
   wherein when the radiation image detecting device is in the state of receiving a radiographing reservation from the control terminal apparatus, the radiation image detecting device having the reception control section does not receive another radiographing reservation.

6. The radiographing system of claim 1, comprising:
   a plurality of radiation image detecting devices;
   a plurality of control terminal apparatuses for selecting a radiation image detecting device to be used among the plurality of radiation image detecting devices,
   wherein when the radiation image detecting device is in the state of receiving a radiographing reservation from one of the control terminal apparatuses, the radiation image detecting device having the reception control section does not receive another radiographing reservation.

7. The radiographing system of claim 1,
   wherein the radiation image detecting device cancels the state of receiving after completion of radiographing of the received radiographing reservation.

8. The radiographing system of claim 1,
   wherein the radiation image detecting device transmits radiation image data to the control terminal apparatus whose radiographing reservation has been received, after completion of radiographing of the received radiographing reservation.

9. A radiation image detecting device for acquiring radiation image data based on a radiation having passed through a subject, the radiation image detecting device being connected with a control terminal apparatus through a communication line and comprising:
   a radiographing reservation receiving section for receiving a radiographing reservation from the control terminal apparatus;
   a radiographing condition control section for setting a reception state to be a state of receiving when the radiographing reservation receiving section receives a radiation reservation; and
   a reception control section for controlling acquisition of radiation image data related to a radiographing reservation which the radiographing reservation receiving section has received, wherein when the reception state is the state of receiving, the reception control section does not receive another radiographing reservation.

10. The radiation image detecting device of claim 9, further comprising:
    a receiving section for receiving a radiographing reservation and a control terminal ID for identifying the control terminal apparatus;
    a storage section for storing the control terminal ID identifying a control terminal apparatus whose radiographing reservation has been received,
    wherein when the receiving section receives a control terminal ID different from the control terminal ID stored in the storage section, the reception control section does not receive such a radiographing reservation which is received from the control terminal apparatus which has a control terminal ID different from the control terminal ID stored.

11. The radiation image detecting device of claim 9,
    wherein the radiographing condition control section cancels the reception state of receiving after acquiring the radiation image data.

12. The radiation image detecting device of claim 9, further comprising,
    transmitting radiation image data, and
    wherein the radiographing condition control section cancels the reception state of receiving after the transmission section transmits the radiation image data.

* * * * *